(12) United States Patent
Gojobori et al.

(10) Patent No.: US 7,003,440 B2
(45) Date of Patent: Feb. 21, 2006

(54) METHOD, SYSTEM, AND PROGRAM FOR USE IN DISPLAYING EXPRESSION PHENOMENON IN LIVING MATTERS

(75) Inventors: Takashi Gojobori, 10-2, Higashi-ichoda, Mishima-shi, Shizuoka 411-0026 (JP); Yuzuru Tanaka, Hokkaido (JP); Toshitsugu Okayama, Shizuoka (JP)

(73) Assignee: Takashi Gojobori, Shizuoka (JP)

( * ) Notice: Subject to any disclaimer, the term of this patent is extended or adjusted under 35 U.S.C. 154(b) by 99 days.

(21) Appl. No.: 10/088,550

(22) PCT Filed: Jul. 13, 2001

(86) PCT No.: PCT/JP01/06087

§ 371 (c)(1),
(2), (4) Date: Mar. 13, 2002

(87) PCT Pub. No.: WO02/07100

PCT Pub. Date: Jan. 24, 2002

(65) Prior Publication Data

US 2002/0150941 A1    Oct. 17, 2002

(30) Foreign Application Priority Data

Jul. 13, 2000 (JP) ............................. 2000-213106
Feb. 1, 2001 (JP) ............................. 2001-025933

(51) Int. Cl.
*G06G 7/48* (2006.01)

(52) U.S. Cl. ..................................... 703/11; 702/19
(58) Field of Classification Search ................ 702/19, 702/22; 435/4; 364/578; 703/11
See application file for complete search history.

(56) References Cited

U.S. PATENT DOCUMENTS

| 5,598,350 | A |  | 1/1997 | Kawanishi | ............... 364/496 |
| 6,096,510 | A | * | 8/2000 | Hochman | ............... 435/29 |
| 6,218,114 | B1 |  | 4/2001 | Peck | ............... 435/6 |
| 6,308,170 | B1 | * | 10/2001 | Balaban | ............... 707/3 |
| 2002/0068269 | A1 | * | 6/2002 | Allen et al. | ............... 435/4 |

FOREIGN PATENT DOCUMENTS

| EP | 0 463 951 A3 | 2/1992 |
| JP | 2000163396 | 6/2000 |

OTHER PUBLICATIONS

U.S. Appl. No. 60/188,168.*

(Continued)

*Primary Examiner*—Ardin H. Marschel
*Assistant Examiner*—Jerry Lin
(74) *Attorney, Agent, or Firm*—Reed Smith LLP; Stanley P. Fisher, Esq.; Juan Carlos A. Marquez, Esq.

(57) ABSTRACT

A method for use in displaying an expression phenomenon in a living matter that are capable of displaying (printing), in a format directly appealing to the eyes or sense, information indicative of gene expression phenomena occurring with time to assist a researcher with easy elucidation of a gene network mechanism. It comprises memorizing means that memorizes an expression data in a cell unit or a site unit along a time axis; and processing means adapted to visualize and display a gene expression phenomenon on a display screen, and comprises the steps of displaying, as a three-dimensional image on a display screen, a shape of a living matter of a cell or site of which expression phenomenon is observed; setting a viewpoint on a three-dimensional space where the gene expression phenomenon in the shape of the living matter displayed is to be observed; and creating a three-dimensional image representing the expression phenomenon at the set viewpoint or at a fixed viewpoint, to display it in one color or multiple colors in various scales depending on a frequency of expression of a gene in the subject cell or site.

7 Claims, 39 Drawing Sheets

OTHER PUBLICATIONS

Hartenstein, V., Andrew, L. and Toga, A., A graphic digital database of *Drosophila embryogenesis*, Feb. 1995, Trends in Genetics, vol. 11, No. 2, p. 51-58.*

Martinelli, S., Brown C., and Durbin R., Gene expression and development databases for *C. elegans*, Oct. 1997, Seminars in Cell & Developmental Biology, vol. 8, No. 5, p. 459-467.*

Debry, R., and Seldin M., Human/Mouse Homology Relationships, May 1996, Genomics, vol. 33, No. 3, p. 337-351.*

Hartenstein et al. "A Graphic Digital Database of *Drosophila* Embryogenesis " (1995) Trends in Genetics vol. 11, No. 2 (pp. 51-58).*

Olivo et al., "Reconstruction from Serial Selections: A Tool for Development Biology. Application to Hox Genes Expression in Chicken Wing Buds", Bioimaging 1, (1993), pp. 151-158.

Ruffins et al., "Three Dimensional Digital Mouse Atlas Using High Resolution MRI", Society for Neuroscience Abstracts, vol. 26, No. 1-2, (2000), pp. Abstract.

Kiernan et al., "The Expression Domain of Two Related Homeobox Genes Defines a Compartment in the Chicken Inner Ear That May Be Involved in Semicircular Canal Formation", Developmental Biology 191, (1997), pp. 215-229.

* cited by examiner

FIG.3(a)

Gene profile table 301

| Cell ID | Degree of expression of gene 1 | Degree of expression of gene 2 | Degree of expression of gene 3 | ... | Degree of expression of gene n |
|---|---|---|---|---|---|
| Cell ID | Degree of expression of gene 1 | Degree of expression of gene 2 | Degree of expression of gene 3 | ... | Degree of expression of gene n |
| Cell ID | Degree of expression of gene 1 | Degree of expression of gene 2 | Degree of expression of gene 3 | ... | Degree of expression of gene n |

Time axis ↓

Cleavage table 302

| Cell ID | Division stage | Child cell ID1 | Child cell ID 2 |
|---|---|---|---|
| Cell ID | Division stage | Child cell ID1 | Child cell ID2 |
| Cell ID | Division stage | Child cell ID1 | Child cell ID2 |

3021, 3022, 3023, 3024

Shape data

[Shape]

[Content of shape data] 3048

VERTICES
1: (0, 1, 0)
2: (0, 0, 1)
3: (1, 0, 0)
4: (0, 0, 0)
5: (0, -1, 0)
END
FACES
<1, 2, 3>
<1, 3, 4>
<1, 4, 2>
<2, 5, 3>
<3, 5, 4>
<2, 4, 5>
END

Gene map table

Expression profile is single point in N-dimensional space with degrees of expression of respective genes used as axes.

Mapping where relation in magnitude of distances conserved

METHOD, SYSTEM, AND PROGRAM FOR USE IN DISPLAYING EXPRESSION PHENOMENON IN LIVING MATTERS

RELATED APPLICATIONS

This application is a 371 of PCT JP01/06087, filed Jul. 13, 2001, and claims priority to Japanese Application Serial No. 25933/2000, filed Feb. 1, 2001 and Japanese Application Serial No. 213106/2000 filed Jul. 13, 2000.

TECHNICAL FIELD

The present invention relates to a method, a system, and a program for use in displaying an expression phenomenon in a living matter that is adapted to visually display (or visually print), as a three-dimensional image, the expression phenomenon of genes (nucleic acid sequences, amino acid sequences, or derivatives thereof) in one or more living matters.

BACKGROUND OF ART

Elucidation of gene expression in living matters is the most fundamental issue in applied sciences including, from unraveling an onset mechanism of disorders and development of new medical drugs, to food engineering. It is known that many genes are involved even in a certain phenomenon and a complicated network is formed among these genes.

The network is formed chronologically in three-dimensional space through transmission of stimuli caused by the release of a chemical substance to adjacent tissues, rather than being found locally in a single tissue.

On the other hand, experimentally observed data are discrete ones indicating frequency of expression of genes in each cell in each tissue at a certain instance in time.

Conventionally, analysis of expression profiles in living matters measures frequency of substances expressed (the number of molecules expressed) in isolated cell or tissue samples and the measurements are used as individual data or two-dimensional tabular data. Analytical systems used therefore can only graph out separately chronological changes of a given tissue or a given gene to observe the expression phenomenon as a map in the space obtained by scaling down coordinate dimensions.

With such analytical systems or methods, there is no way of adding in information indicative of proximity of cells or tissues. Even in the case where a gene A discovered in a cell causes expression of a gene B in an adjacent tissue, they are correlated just as one among others in the data and it is very difficult to determine an association therebetween.

More specifically, it is very difficult to elucidate a mechanism of coordinated expression directly from raw data in an analytical procedure that does not add in effects of any factors such as spatial and proximity information and that does not use any visualization technique evoking imaginations of an observer on a three-dimensional image. An approach that covers these shortcomings includes an in vivo staining experiment technique to observe a real organism directly rather than through analysis of data.

This is an approach to hybridize DNA of a gene to be analyzed with a directly labeled complementary DNA to visualize a frequency of expression based on the intensity of the label, which allows three-dimensional observation of how an expression proceeds in a living matter by changing viewpoints.

However, the above-mentioned in vivo staining experiment technique requires separate experiments for a single expression DNA or individual pairs of expression DNAs to be detected. In addition, suitable organisms for the staining experiment are limited to primitive translucent ones such as nematodes and *Tardigrada* of which label can be observed with a transmission light source. The technique cannot be applied to analysis of expression information on higher organisms including human. Thus, the problem exists that it is unable to elucidate a network mechanism of gene expression in the higher organisms.

The present invention is made with respect to problems in the prior art. An object thereof is to provide a method and a system for use in displaying an expression phenomenon in a living matter that are capable of displaying (printing), in a format directly appealing to the eyes or sense of a researcher, information indicative of gene expression occurring with time to assist the researcher with easy elucidation of a gene network mechanism.

DISCLOSURE OF THE INVENTION

In order to achieve the above-mentioned objects, the present invention comprises memorizing means that memorizes, in a cell unit or a site unit of the living matter along a time axis, data indicative of a shape thereof and an expression data associated with the degree of gene expression; and processing means adapted to obtain the data indicative of the shape and expression data that are memorized in the memorizing means to visualize and display the gene expression phenomenon on a display screen, which is characterized by comprising a first step of displaying as a three-dimensional image on the display screen a shape of the living matter of a cell or site of which expression phenomenon is observed; a second step of setting a viewpoint in a three-dimensional space where the gene expression phenomenon in the shape of the living matter displayed is to be observed; and a third step of reading the gene expression data of the cell or the site in the shape of the living matter out of the memorizing means, creating a three-dimensional image representing the expression phenomenon at the viewpoint set at the second step or at a fixed viewpoint, to display it in one color or multiple colors in various scales depending on a frequency of expression of a gene in the subject cell or site.

In addition, it is characterized by chronologically displaying a change in shape of a cell or site associated with embryogenesis of gene expression; and displaying as an animation a change of a three-dimensional image representing an expression phenomenon from a certain viewpoint at a certain instant of time.

It is characterized by chronologically displaying a change in shape of a cell or site of the living matter caused by an external stimulation or a change in shape of a cell or site caused by the living activities of its own; and displaying as an animation a change of a three-dimensional image representing an expression phenomenon from a certain viewpoint at a certain instant of time.

It is also characterized by displaying in parallel three-dimensional images representing expression phenomena for each cell or site of two or more living matters.

It is characterized by comparing the three-dimensional images representing expression phenomena for each cell or site of two or more living matters to visually display similarities therebetween in a predetermined display format.

It is characterized by mapping an expression data of a cell or site to be observed on coordination points in a color space of the three primary colors which is based on a data value thereof to display it as color information corresponding to the individual coordination points.

It is characterized by mapping expression data of two or more cells or sites on coordination points in a color space of the three primary colors which is based on data values thereof to display them in parallel as color information corresponding to the individual coordination points.

It is characterized by cutting imaginarily a three-dimensional image representing the expression phenomenon displayed, at a plane or a curved plane designated in a three-dimensional space to display an image representing the expression phenomenon along the cutting plane.

It is characterized by displaying information about the gene expressed in a designated cell or site as a string of characters or as graphics, in response to an operation that designates the cell or site on a three-dimensional image representing the expression phenomenon displayed.

It is characterized by coordinating a three-dimensional image representing the expression phenomenon with a pedigree diagram (tree structure) on embryogenesis for display.

It is characterized by displaying a three-dimensional image representing the expression phenomenon in the designated cell, in response to an operation that designates a cell on the pedigree diagram.

It is characterized by displaying a three-dimensional image representing the expression phenomenon in the designated cell before and after differentiation, in response to an operation that designates a cell on the pedigree diagram.

It is characterized by displaying expression data of a designated cell as a string of characters or as graphics, in response to an operation that designates a cell on the pedigree diagram.

It is characterized by coordinating and displaying, in a predetermined display format, a three-dimensional image of the expression phenomenon and a position of a gene on a gene map that causes expression.

It is characterized by coordinating and displaying, in a predetermined display format, three-dimensional images of the expression phenomenon of a gene in two or more cells or sites and a position of a gene on a gene map that causes expression.

A system according to the present invention is characterized by comprising first memorizing means that memorizes, in a cell unit or a site unit of a living matter, data indicative of a shape thereof along a time axis; second memorizing means that memorizes an expression data associated with the degree of expression of a gene along a time axis; first processing means adapted to obtain the data indicative of the shape memorized in the first memorizing means to display, on the display screen as a three-dimensional image, a shape of the living matter at the cell or site where the expression phenomenon is to be observed; viewpoint setting means for setting a viewpoint in a three-dimensional space to observe the expression phenomenon in the shape of the living matter displayed; second processing means adapted to read the data about the gene expression at the cell or site in the shape of the living matter out of the second memorizing means to create a three-dimensional image representing an expression phenomenon at the viewpoint set by the viewpoint setting means or at a fixed viewpoint, thereby displaying it in one color or multiple colors depending on a frequency of expression of the gene in the subject cell or site.

In addition, it is characterized in that the system is configured with separate computers in which a computer that manages the first and second memorizing means is connected via a network with a computer comprising the first and second processing means.

It is characterized in that the system is configured with separate computers in which a computer comprising the second memorizing means is connected via a network with a computer comprising the first memorizing means as well as the first and second processing means.

It is characterized in that the first and second memorizing means and the first and second processing means are stored in a single computer or are distributed among and stored in two or more computers connected with each other via a network.

Furthermore, provided is a system comprising a client computer and a server computer connected to each other via a network, the system being adapted to visualize an expression phenomenon in a gene to display it on a display screen on the client computer in response to a request from the client computer, the system being characterized in that the server computer comprises first memorizing means that memorizes, in a cell unit or a site unit of a living matter, data indicative of a shape thereof along a time axis; second memorizing means that memorizes an expression data associated with the degree of expression of a gene along a time axis; first processing means adapted to receive, from the first memorizing means, the data indicative of the shape of the living matter required by the client computer and create a three-dimensional image of the shape of the living matter at the cell or site where the expression phenomenon is to be observed, to send it back to the requesting client computer; and second processing means adapted to receive, from the second memorizing means, data indicative of expression of the gene at the cell or site in the shape of the living matter produced as the three-dimensional image sent to the client computer, in response to information received from the client computer about a viewpoint in a three-dimensional space where the expression phenomenon in the shape of the living matter is to be observed, and create a three-dimensional image in one color or multiple colors in various scales, the image representing the expression phenomenon at the viewpoint designated by the information about the viewpoint or at a fixed viewpoint, to send it back to the requesting client computer; the client computer comprising first designation means for designating a living matter to be observed; second designation means for designating a viewpoint in a three-dimensional space where an expression phenomenon is to be observed; and display means for displaying a three-dimensional image representing a shape of the living matter and a three-dimensional image representing the expression phenomenon, that are received from the server computer.

Moreover, it is characterized in that either one or both of the first and second memorizing means is/are included in a different server computer from the above-mentioned server computer.

BRIEF DESCRIPTION OF THE DRAWINGS

FIG. 3 is a view illustrating a configuration of a gene database;

BEST MODE FOR CARRYING OUT THE INVENTION

An embodiment of the present invention is described below with reference to the drawings.

First, an example is given where the present invention is implemented to simulate development of an organism and then extension to biological tissues is described.

Figure 1:
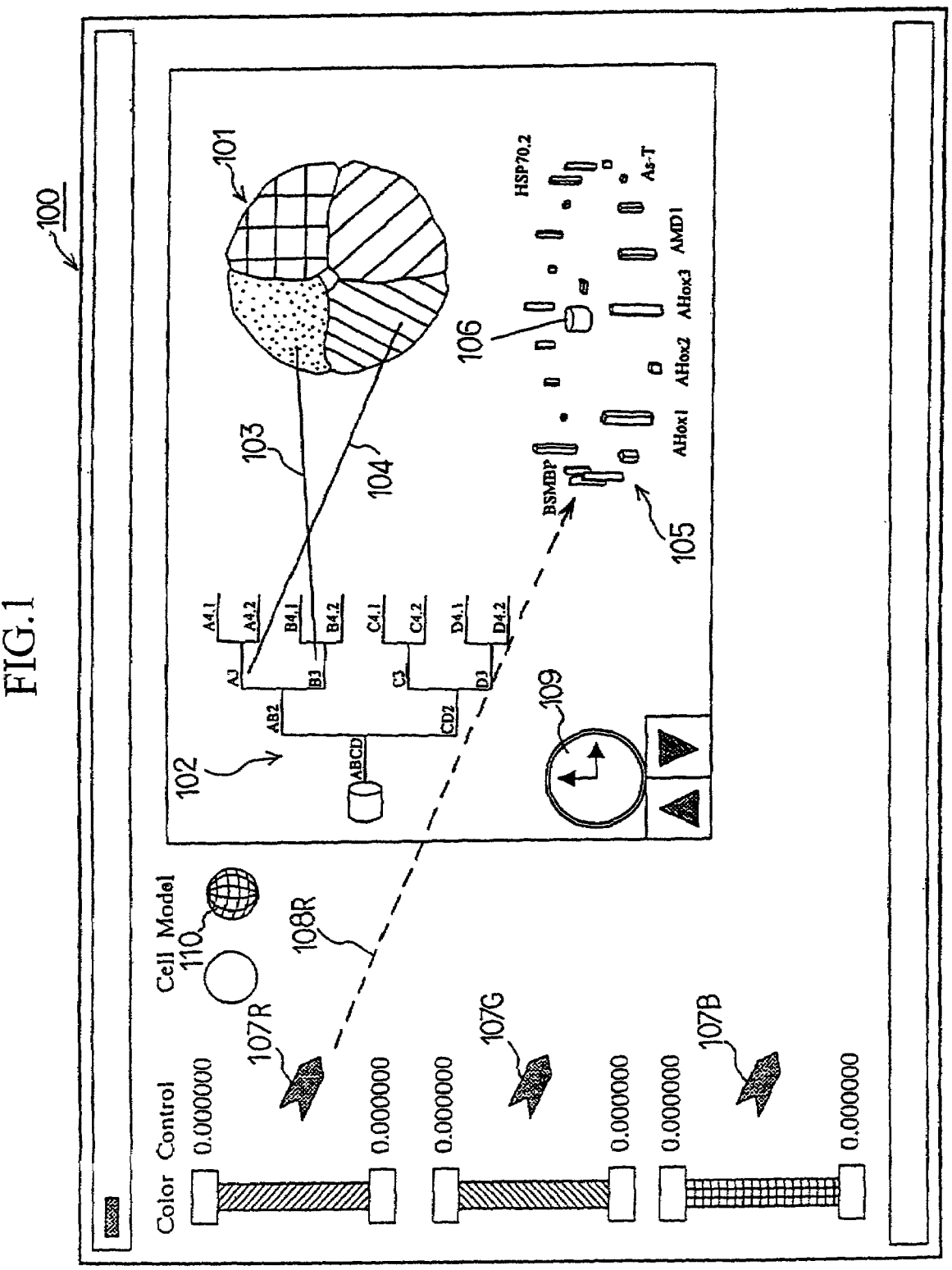
FIG. 1 shows a display screen achieved by a method for displaying an expression phenomenon according to the present invention.

FIG. 1 shows a display screen achieved by a method for displaying an expression phenomenon according to the present invention. A three-dimensional shape 101 of a fertilized egg (illustrated at the eight-cell stage) a living matter is displayed at the approximate center of a display screen 100. The three-dimensional shape 101 of the fertilized egg is changed to a shape at a designated stage when the stage of cleavage is designated. A reference numeral 102 is a cleavage transition tree representing transition of the cleavage in a hierarchical manner. Nodes (e.g., ABCD, AB2, CD2) in the cleavage transition tree 102 each corresponds to a cell, indicating how the cell divides through the cleavage. The cells forming a single three-dimensional shape 101 illustrated are each connected to their respective corresponding nodes in the cleavage transition tree 102 through line segments 103 and 104 to indicate the relationship between the cells and the nodes.

Choosing a stage in the cleavage transition tree 102 by, for example, clicking it with a mouse displays the three-dimensional images 101 of the fertilized egg in the transition process of the cleavage to that stage on separate windows or on the same window in a parallel manner. The stages as used herein mean those in the process of development of an individual, which is the stages of the cleavage in this embodiment. Choosing a node in the cleavage transition tree 102 by, for example, clicking it with a mouse changes the display of the three-dimensional images 101 of the fertilized egg into the three-dimensional image at the corresponding stage. When the distance from the root to a leaf in the cleavage transition tree 102 is large, it is difficult to display the nodes at the levels of the leaves on a single window due to the limitation of the screen width. In order to solve this problem, the present embodiment has a function to offset the planes where the nodes are expanded by π/2 for each level in the hierarchy.

The three-dimensional shape 101 of the fertilized egg and the cleavage transition tree 102 are used as a user interface (UI) to allow designation of the cell. Choosing a cell on the three-dimensional shape 101 or in the cleavage transition tree 102 by, for example, clicking it with a mouse displays a gene profile (gene list) 105 of that cell as a cylindrical graph. In this example, the cylindrical graph is displayed along the circumferential path as illustrated, to provide effective use of the screen. The cylindrical graph can be rotated for display to any position on the circumference. When a string of characters representing a name of a gene (e.g., Ahox1, AMD1, and As-T) is overlapped and is illegible in the gene profile 105, the cylindrical graph may be rotated clockwise by clicking the rotation center 106 of the cylindrical graph to the left direction or rotated counter-clockwise by clicking it to the right direction, to display the name of the gene of interest at or near the left or right end on the rotation circumference for confirmation.

Reference numerals 107R to 107B are icons that serve as a user interface for assigning the three primary colors R (red), G (green), and B (blue) to the genes to display in color the gene profiles of three genes, and are corresponding to R, G, and B from the top. Colors can be assigned to the gene names corresponding to the cylindrical graph by means of connecting the arrowhead-shaped icons 107R to 107B through line segments to the cylindrical bars of the cylindrical graph for the gene profile 105 using a mouse. For example, connecting the icon 107R for R to the cylindrical graph for the gene name BSMBP through a line segment 108R assigns the display color red to the gene name BSMBP. The gene name assigned in this way is displayed as a string of characters near the icon 107R. The function of assigning the display color to the given gene name makes it possible to display the three-dimensional shape and the nodes in the cleavage transition tree using the colors obtained by converting the amount proportional to the degree of expression of the three different genes into the brightness of R, G, and B.

Figure 2:
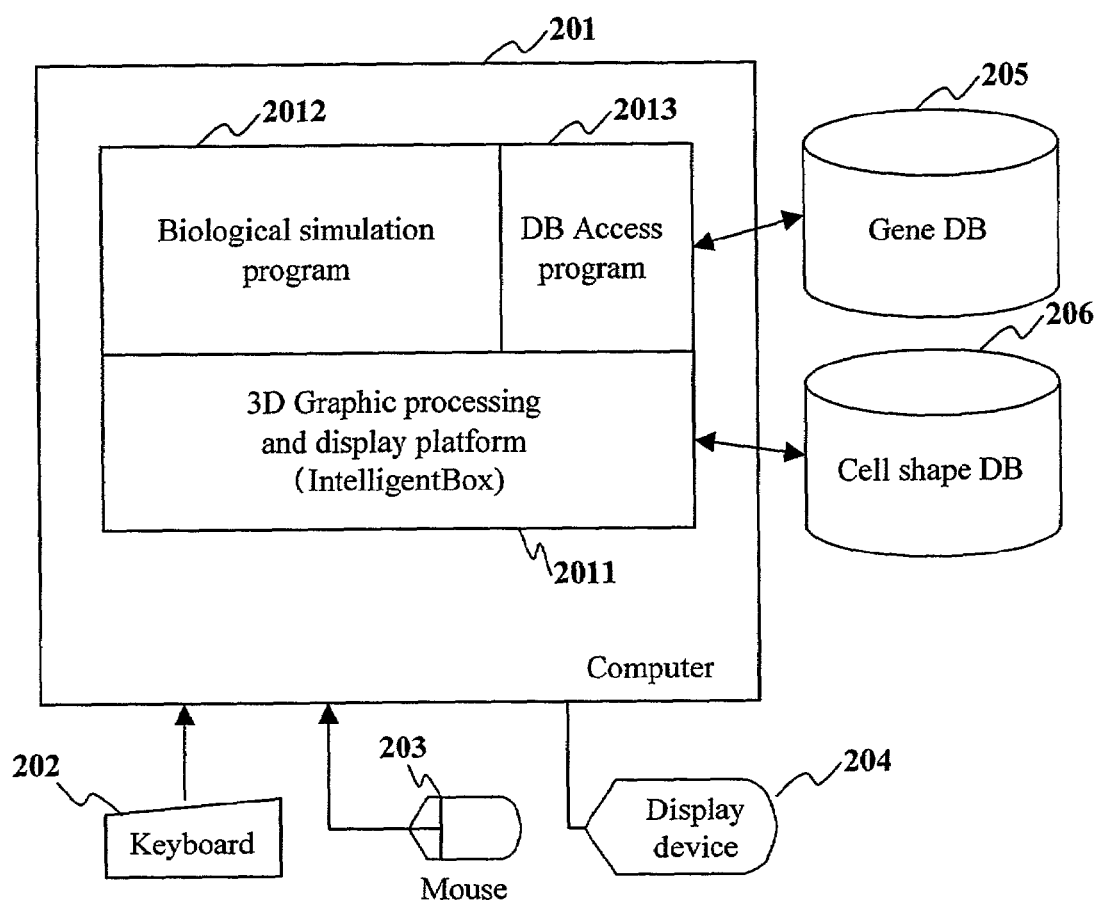
FIG. 2 is a configuration diagram showing an embodiment of a system implementing the present invention.

FIG. 2 is a block diagram showing a configuration of an embodied system for displaying a gene expression phenomenon where the present invention is implemented. It comprises a computer 201 to which a keyboard 202, a mouse (pointing device) 203, and a display device 204 are connected, a gene database (DB) 205, and a cell shape database (DB) 206. Either one or both of the databases 205 and 206 may be located at a remote site from the computer 201 as long as they are accessible from the computer 201. The database(s), when located at a remote site from the computer 201, may be configured to be accessible through a network or the Internet.

The computer 201 is configured with a three-dimensional graphic processing and display platform 2011, for example, "IntelligentBox" on which installed are a biological simulation program 2012 and a DB access program 2013 for accessing the gene DB 205. Details of the IntelligentBox can be found in, Yoshihiro Okada and Yuzuru Tanaka, "IntelligentBox: A Constructive Visual Software Development System for Interactive 3D Graphic Applications", Computer Software, Japan Society for Software Science and Technology, Vol. 12, No. 4, pp. 84–94, 1994; Yoshihiro Okada and Yuzuru Tanaka, "IntelligentBox: A constructive Visual Software Development System Interactive 3D Graphics Applications", Proceedings of the Computer Animation 1995 Conference, IEEE, Computer Society; Yoshihiro Okada, "Collaborative Environments in 3D Software Development System called IntelligentBox", Computer Software, Japan Society for Software Science and Technology, Vol. 14, No. 1, pp. 3–14, 1997; and Yoshihiro Okada and Yuzuru Tanaka, "Collaborative Environments of IntelligentBox for Distributed 3D Graphic Applications", Proceedings of the Computer Animation '97, IEEE Computer Society. Since processing and display of the three-dimensional graphics herein are completely based on the IntelligentBox system in this example, description about the process is omitted in this embodiment section.

FIGS. 3 to 5 illustrate a configuration of the gene database (DB) 205. The gene database 205 stores various tables including a gene profile table 301 and a cleavage table 302 from which information about genes or cells can be obtained according to a name of a gene or a cell ID. FIG. 3 shows the gene profile table 301 and the cleavage table 302.

The gene profile table 301 shown in FIG. 3(a) contains, along a time axis, a cell ID 3011 and data 3012 to 301n about the degree of expression of the n number of "GENE 1" to "GENE n" in the subject cell for each cell ID. The cleavage table 302 shown in FIG. 3(b) contains a cell ID 3021, a division stage 3022, a "CHILD CELL ID 1" 3023, and a "CHILD CELL ID 2" 3024, for each cell ID.

On the other hand, the cell shape database 206 stores a cell shape table 303, a site shape table 304, and a gene map table 305, as shown in FIGS. 4 and 5.

Figure 4A:
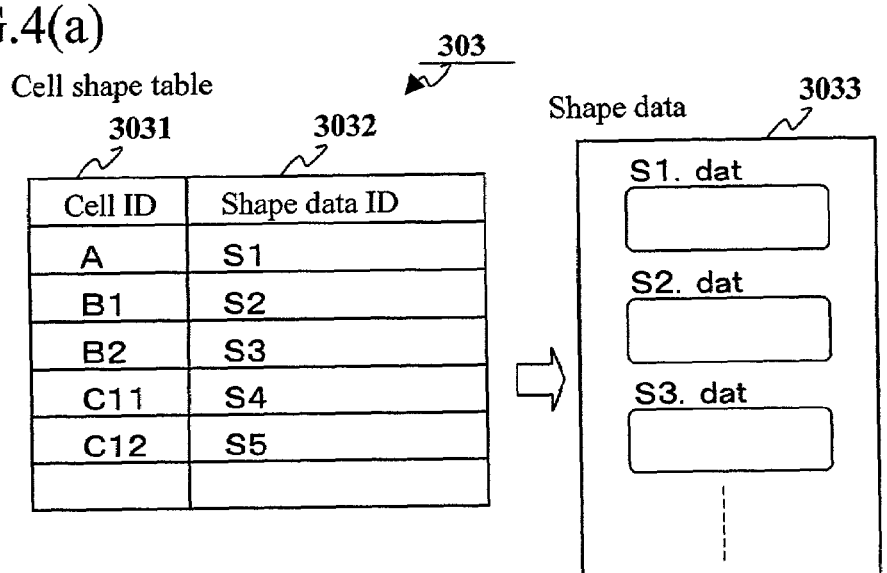
FIG. 4 is a view illustrating a configuration of a cell shape database.

The cell shape table 303 contains an cell ID 3031 and a shape data ID 3032 as shown in FIG. 4(a) to allow retrieval of a polygon data (shape data) 3033 representing the three-dimensional shape of the subject cell according to the cell ID 3031, and display the three-dimensional shape of the cell specified by the cell ID 3031.

For example, the shape of the cell A having the cell ID=A is represented by the shape data ID=S1 and the shape data thereof is stored in a file S1.dat with the extension "dat".

Figure 4B:
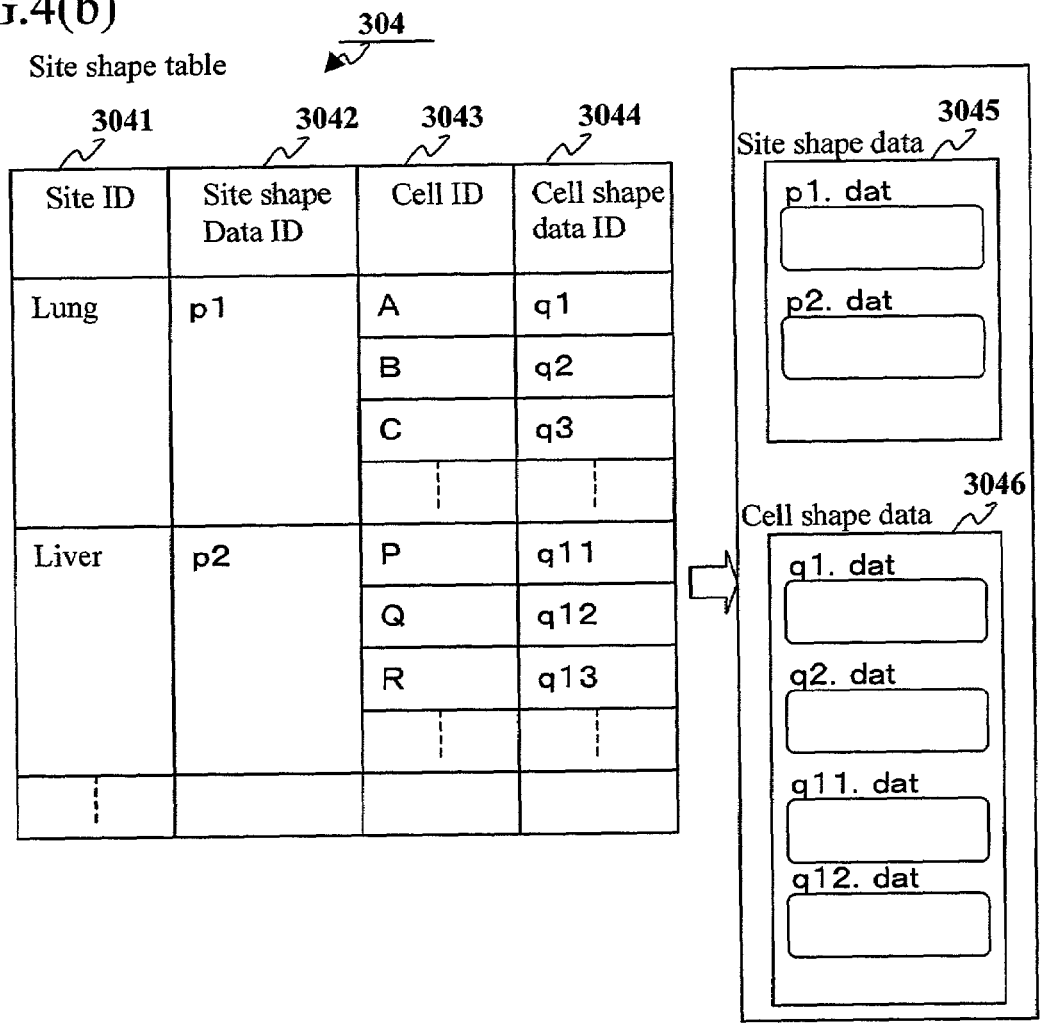

When the site to be observed contains a number of cells, the site shape table 304 is stored that contains two or more pairs of data for the sites such as a lung or a liver, in which a single pair of data for each site ID 3041 consists of site shape data IDs 3042 forming the subject site, cell IDs 3043 for the cells contained in the subject site, and cell shape data 3044, as shown in FIG. 4(b). A site shape data 3045 can be retrieved according to the site ID 3041 to display the three-dimensional shape of the entire site observed. In addition, shape data 3046 for the cells that are present within the subject site are retrieved according to the cell shape data ID 3044 to display the shape and the frequency of expression of each cell in the site observed. In the example shown in FIG. 4(b), the cell forming the lung site consists of A, B, C, . . . while the shape data for these cells are stored in files "q1.dat", "q2.dat", . . .

The site or cell shape data are those representing a shape of a three-dimensional object, formats of which include, for example, a known data format DXF, IGES, VRML, and OBJ.

Figure 5A:
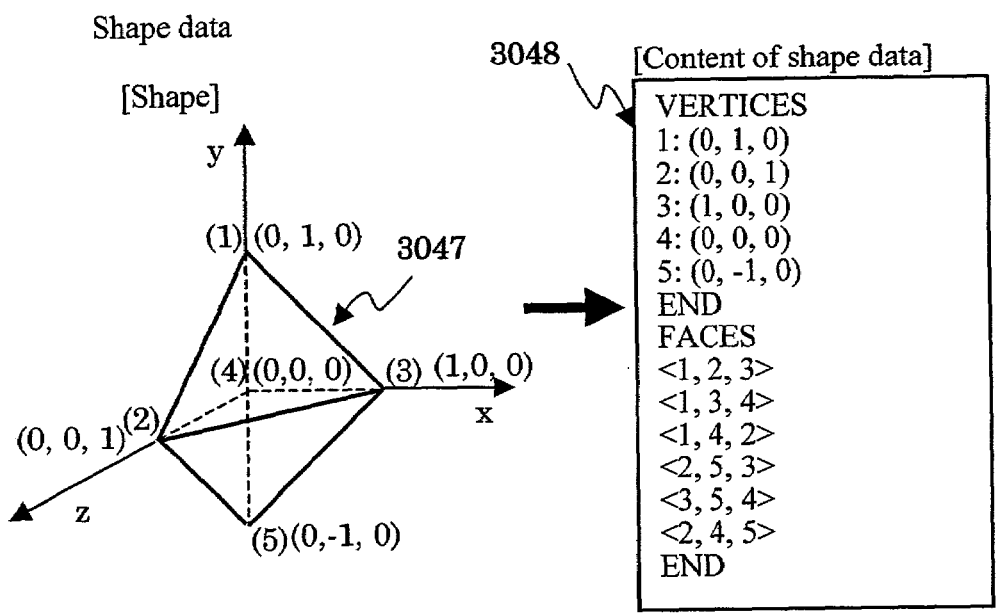
FIG. 5 is a view illustrating shape data and a configuration of a gene map table.

In this embodiment, the shape of an object is approximated by a polyhedron as shown in FIG. 5(a). In FIG. 5(a), a reference numeral 3047 represents a hexahedron placed in a three-dimensional space, with the numerals (1) to (5) indicating vertex numbers. A reference numeral 3048 represents a shape data for the polyhedron 3047. The data between VERTICES and END define three-dimensional coordinates of all vertices. The three-dimensional coordinates of the vertices (1) to (5) are listed along with the vertex numbers. The data between FACES and END define the vertices that form a given face. The vertex numbers that form the subject face are listed counter-clockwise toward the center of the polyhedron for each face thereof. For example, <1, 2, 3> is formed of the vertices (1), (2), and (3).

Alternatively, approximation may be achieved by curved surfaces using a mathematical procedure.

Figure 5B:
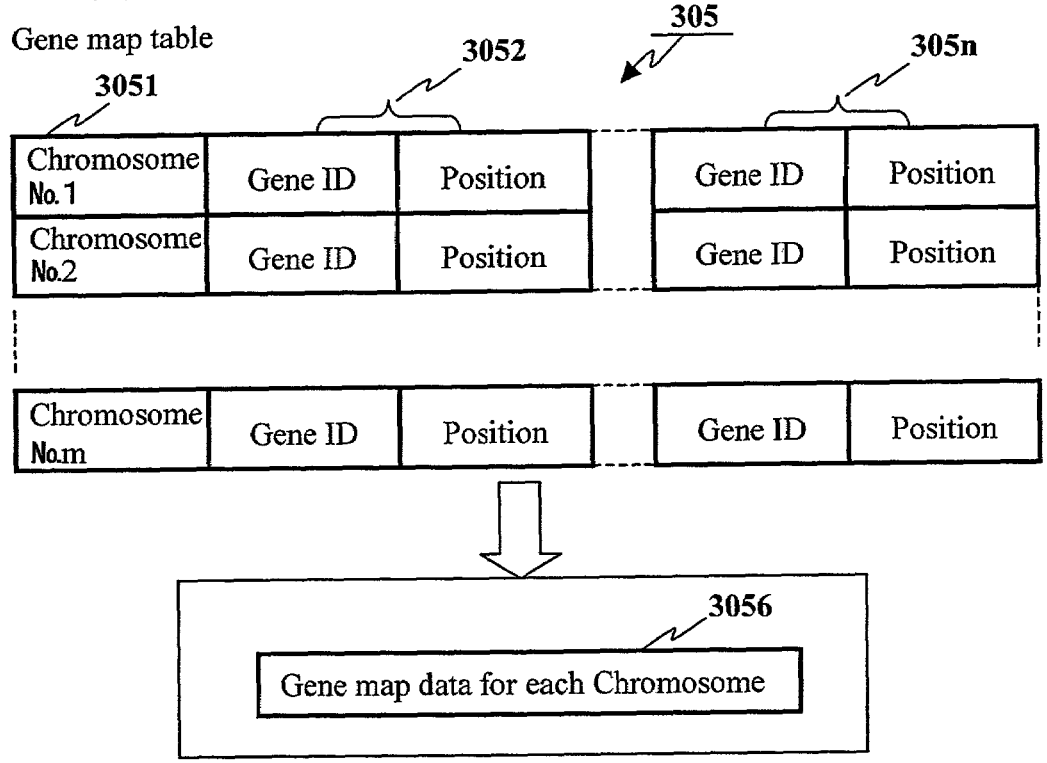

Since a single chromosome contains multiple genes, it is possible to provide gene maps indicating positions of the genes for the given chromosome. To indicate a particular position of a gene on the gene map, the gene map table 305 is provided for each chromosome No. 3051, that contains gene position information 3052 to 305n each consisting of gene IDs and position data in the subject chromosome, as shown in FIG. 5(b). A gene map data 3056 is retrieved for each chromosome to display the gene map represented by the gene map data 3056 of interest. The positions of the gene can thus be displayed on the map.

The position of the gene used herein is an index representing a location of a gene positioned according to a distance on the gene map. The gene distance may be defined in two ways, that is, as a classical genetic distance (a distance given by centi-Morgan or a crossing-over unit) that is measured by experimental measurements of a crossing-over ratio on the gene map, or the one obtained by means of determining, relative to a genome sequence having a full chromosome length, a sequence encoding for the subject specific gene to determine the position in a molecular biological manner. Both cases use the same concept in that the position of the subject gene on the chromosome is represented quantitatively, which would be a basis of determining the position of the gene on a linear map.

Figure 6:
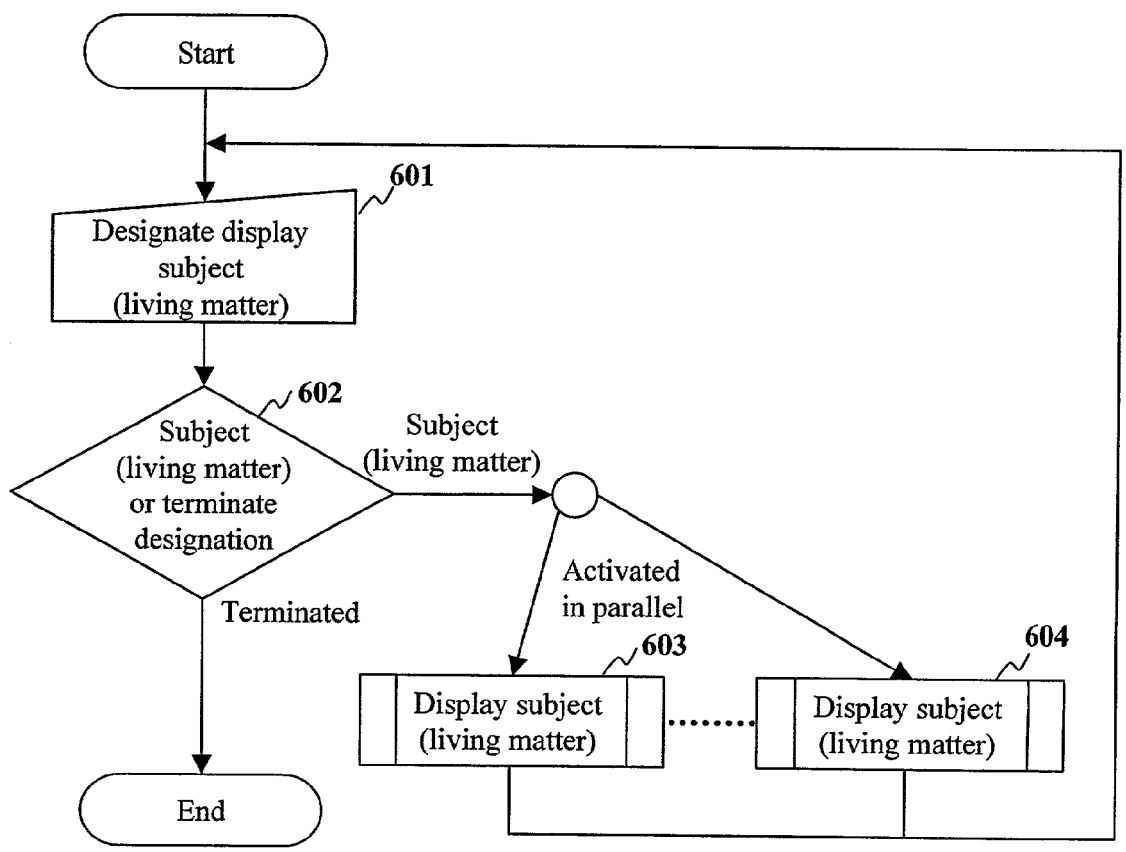
FIG. 6 is a flow chart illustrating a main flow of an operation for displaying an expression phenomenon.

FIG. 6 is a main flow diagram illustrating a general operation carried out in the system shown in FIG. 2. First, at step 601, an observer or an experimenter is inquired to enter an ID (such as a cell ID) of a display subject (living matter) with the keyboard 202 or to enter a request to exit the system. This is determined at step 602. When the request to exit the system is provided, all processes are terminated. However, when an ID of a certain living matter (such as a site of a cell or a living matter), a process to display the subject living matter is activated at steps 603 and 604. Then, the operation returns to the step 601. In this case, when the n number of living matters are designated, the n number of display processes are activated in parallel to display the three-dimensional shapes of the n number of living matters simultaneously.

Figure 7:
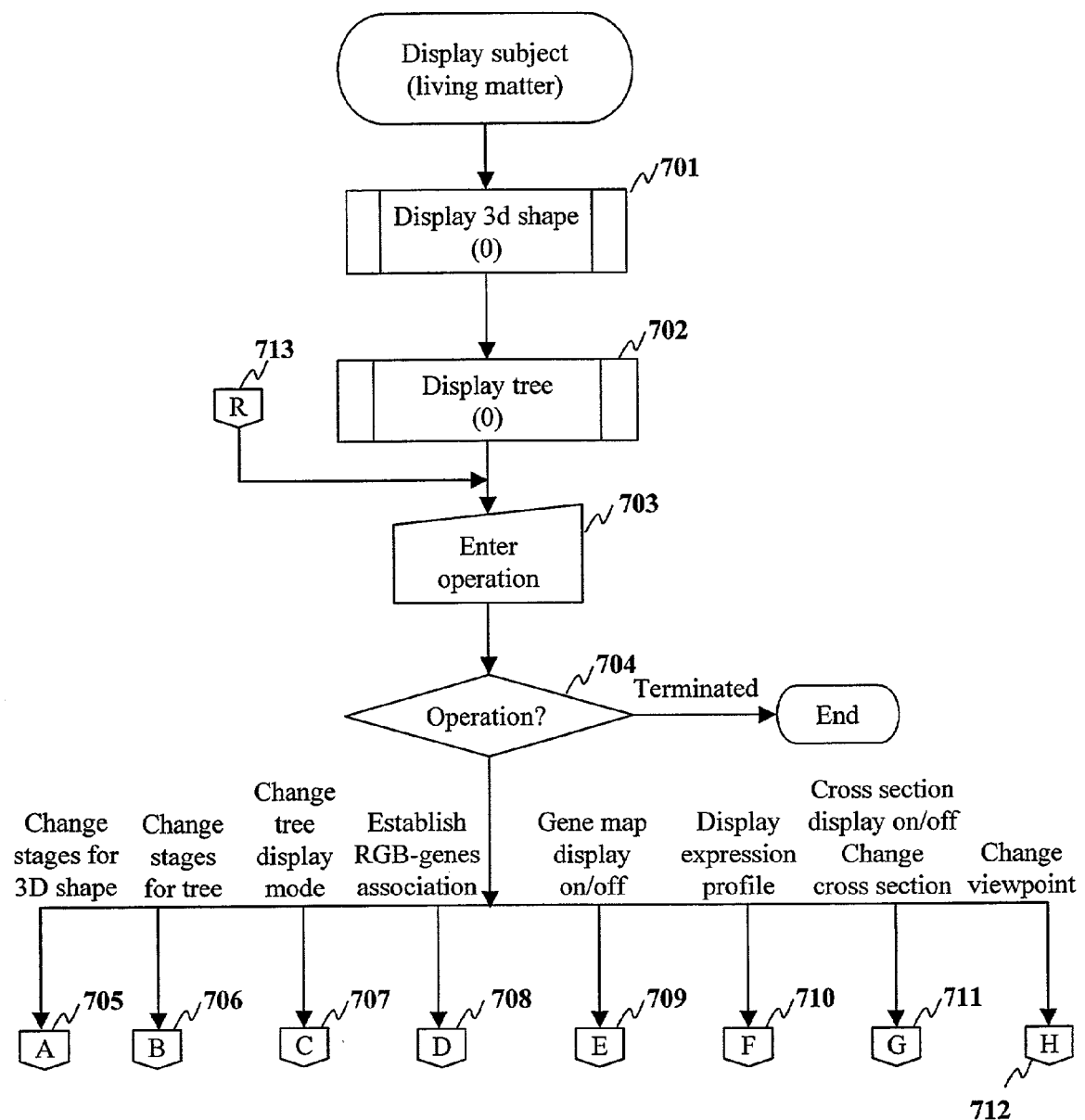
FIG. 7 is a flow chart illustrating a flow of a function for displaying individual subject (organism)

FIG. 7 is a flow chart illustrating functional processes for displaying an expression phenomenon of a given living matter. At step 701, a three-dimensional stereographic shape of the subject living matter at "STAGE 0" is displayed. Next, at step 702, the cleavage transition tree is displayed while keeping the state of the "STAGE 0". At step 703, the observer or the experimenter is inquired to designate a display format. In this case, available designations include the following (1) to (8).

(1) To Change Stages at which Three-Dimensional Shape is Displayed

There are three procedures of moving up (UP) and moving down (DOWN) one level of the cleavage stage, or selecting a node in the cleavage transition tree to directly designate a stage. Details of the process are given from a connector 705 to FIG. 8.

(2) To Change Stages of Cleavage Transition Tree

To change stages of the cleavage transition tree, there are two different procedures of moving up (UP) and moving down (DOWN) one level of the stage. Details of the process are given from a connector 706 to FIG. 9.

(3) To Change Cleavage Transition Tree Display Mode

The cleavage transition tree may be displayed either in a two-dimensional form on a single plane or in a three-dimensional form displayed alternatively according to the levels of the hierarchy on the planes perpendicular to each other, as described above. This procedure is to change it. Details of the process are given from a connector 707 to FIG. 10.

(4) To Establish RGB-Gene Association

An RGB-gene association is established to visualize gene profiles of three genes. Details of the process are given from a connector 708 to FIG. 11.

(5) To Switch SHOW/HIDE of Gene Map Display

This is to switch between show and hide of a view, on a gene map, of a frequency of expression of a gene or genes in a designated cell as brightness information. Details of the process are given from a connector 709 to FIG. 12.

(6) To Display Expression Profile

This is to specify a cell by means of designating a three-dimensional display or a node in the cleavage transition tree, and to display an expression profile thereof as a cylindrical graph. Details of the process are given from a connector 710 to FIG. 13.

(7) To Switch Cross-Sectional View and Change Cross Section

This is to switch between show and hide of a view of a three-dimensional shape in cross section and to change the cross section. Details of the process are given from a connector 711 to FIG. 14.

(8) Change Viewpoint

This is to change a viewpoint of a three-dimensional display to allow observation of the three-dimensional shape at various angles and in various scales. Details of the process are given from a connector 712 to FIG. 15.

Completion of the above-mentioned processes returns the operation to the connector 713. When the exit operation is selected, all processes are terminated.

Details of the respective processes are described below.

Figure 8:
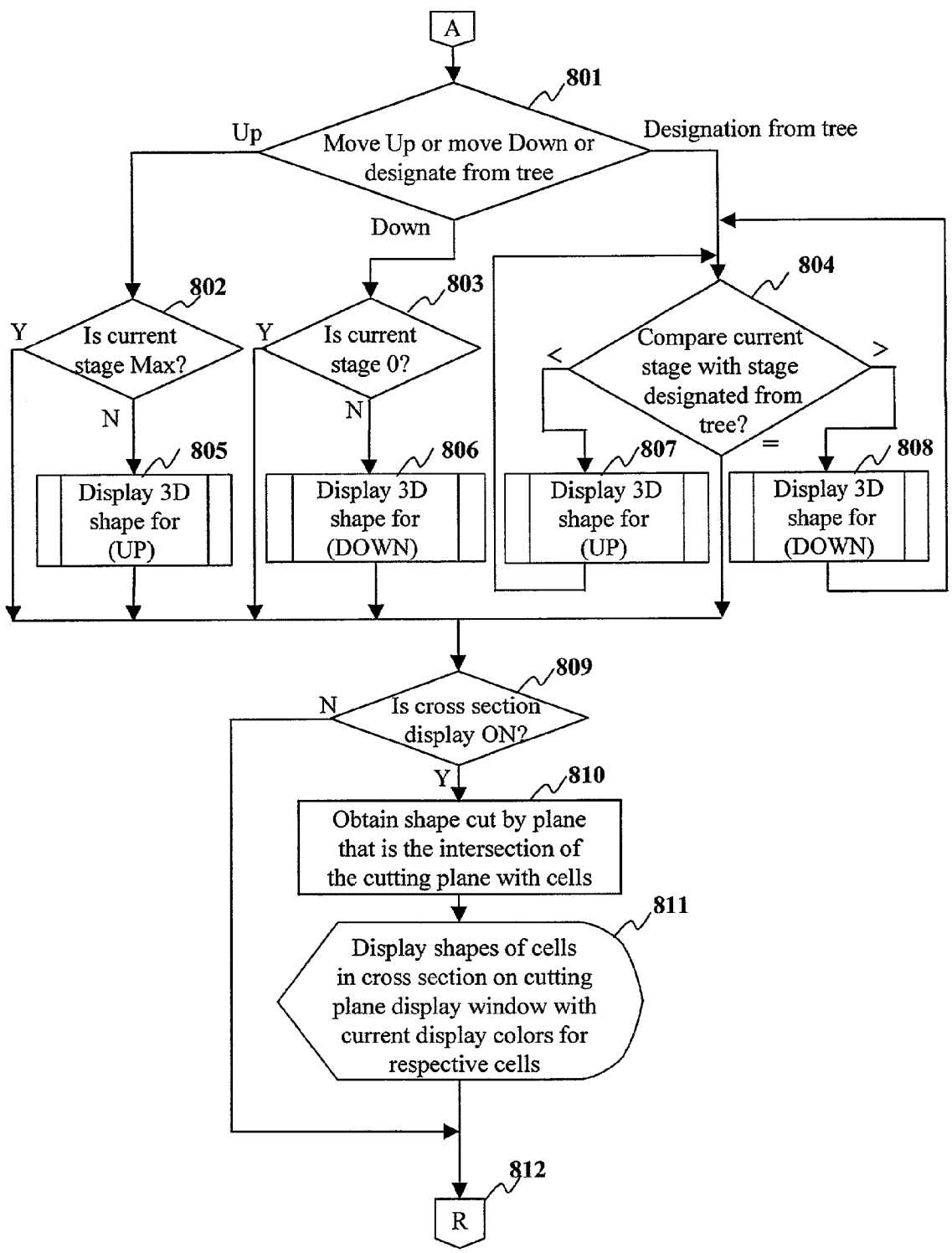
FIG. 8 is a flow chart illustrating details of a process for changing stages for a three-dimensional shape.

First, details of a process for changing the stages for the three-dimensional shape is described with reference to FIG. 8. Here, operation is made to move up or down by one level the stage at which the three-dimensional shape is displayed. Choosing a stage in the cleavage transition tree with a mouse can change the display of the three-dimensional shape to the one at the designated stage. First, at step 801, it is determined whether the operation is to move UP or move DOWN through the stages or to directly select the stage in the cleavage transition tree. If moving UP a stage is selected, it is checked at step 802 whether the current stage is the final stage (Max). If it is the final stage, the process goes to step 809. If not, step 805 calls the process for displaying the three-dimensional shape for UP.

If moving DOWN a stage is selected, it is checked at step 803 whether the current stage is the initial stage (0). If it is the initial stage, the process goes to the step 809. If not, step 806 calls the process for displaying the three-dimensional shape for DOWN.

If the stage is directly designated in the cleavage transition tree, the present embodiment displays the stages on the path one by one to the target stage rather than changing the stage at one time to the designated stage. At step 804, the current stage is compared with the target stage. If the current stage is smaller, step 807 calls the process for displaying the three-dimensional shape for UP. If the current stage is larger at the step 804, step 808 calls the process for displaying the three-dimensional shape for DOWN.

After completion of the above-mentioned operations, the process goes to the step 809 to determine whether the display is made in cross section. If the display is made in cross section, obtained at step 810 is a shape cut by a plane that is the intersection of the cutting plane with cells having a newly displayed three-dimensional shape. The shape is displayed on a cutting plane display window at step 811. The process returns to FIG. 7 through a connector 812. However, if the display is not made in cross section, the process returns to FIG. 7 through the connector 812 without any operation.

Figure 9:
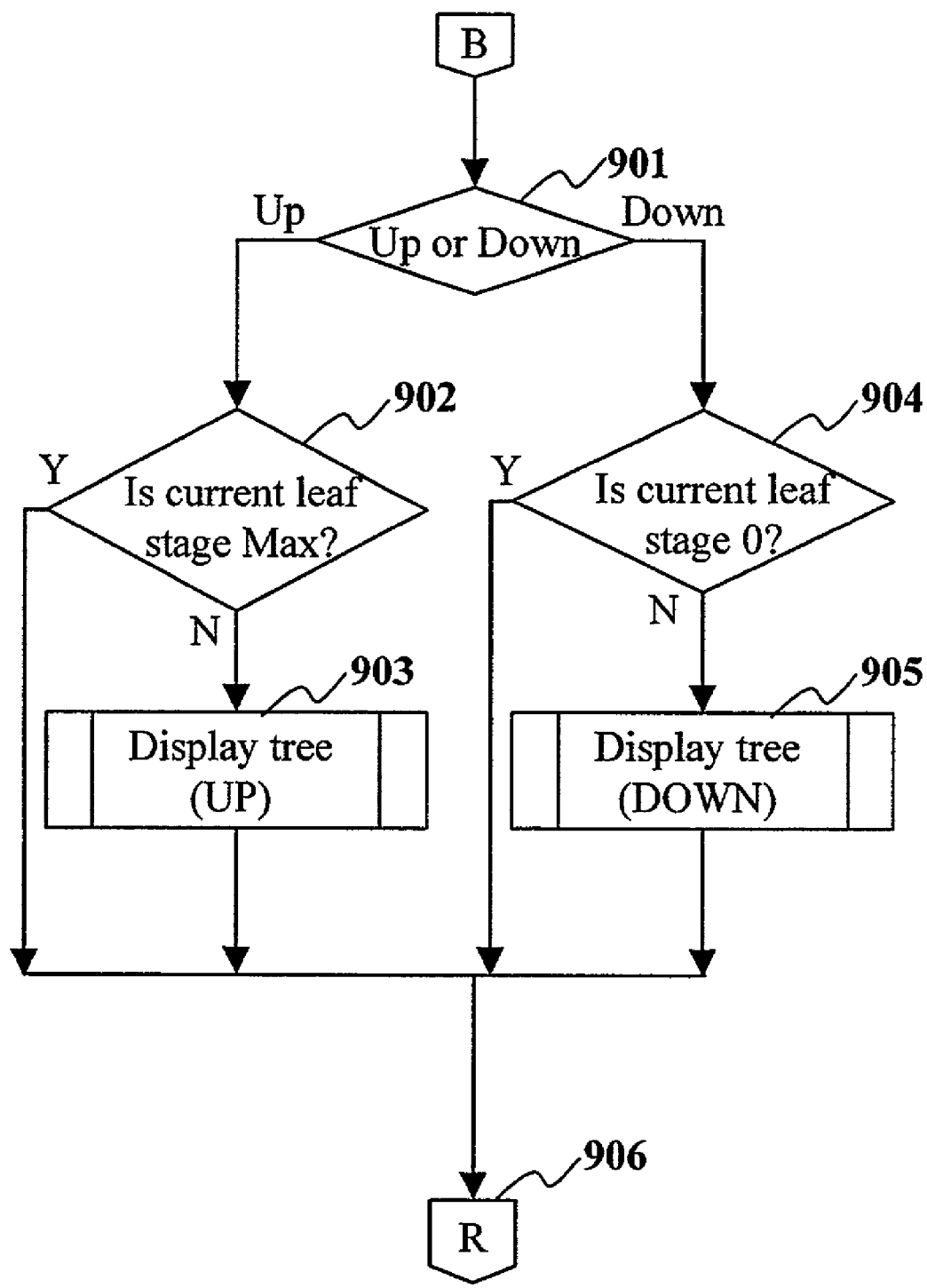
FIG. 9 is a flow chart illustrating details of a process for changing stages for a cleavage transition tree.

Next, a process for changing the stages of the cleavage transition tree is described with reference to FIG. 9. Here, operation is made to move up or down one level of the leaf stage in the cleavage transition tree. At step 901, it is determined whether the operation is UP or DOWN. If UP is selected, it is checked at step 902 whether the current stage is the final stage (Max). If it is the final stage, the process returns to FIG. 7 through a connector 906. If not, step 903 calls the process for displaying the cleavage transition tree for UP and then the process returns to FIG. 7 through the connector 906.

If DOWN is selected, it is checked at step 904 whether the current stage is the initial stage (0). If it is the initial stage, the process returns to FIG. 7 through the connector 906. If not, step 905 calls the process for displaying the cleavage transition tree for DOWN and then the process returns to FIG. 7 through the connector 906.

Figure 10:
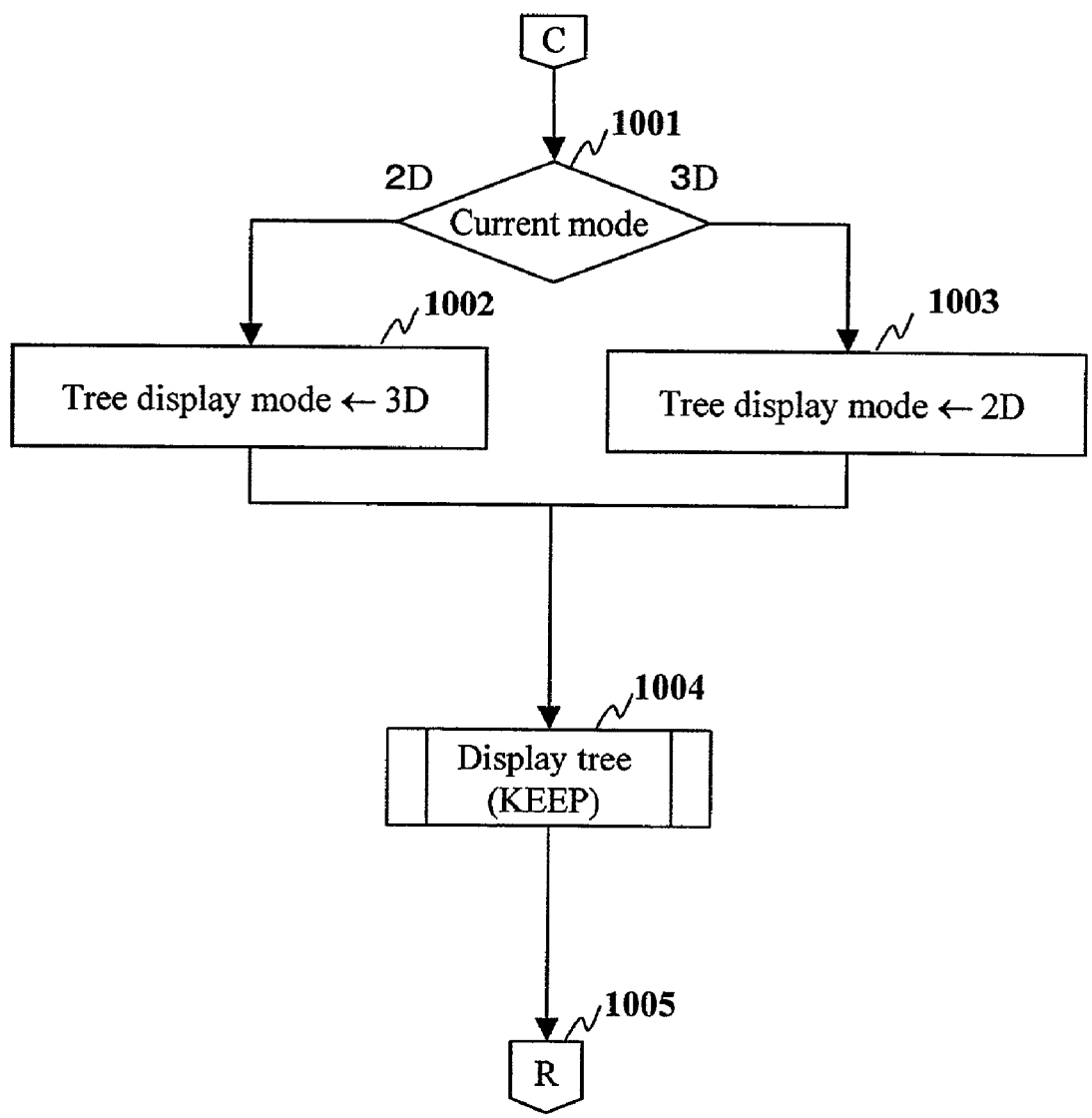
FIG. 10 is a flow chart illustrating details of a process for change a cleavage transition tree display mode.

Next, a process for changing the cleavage transition tree display mode is described with reference to FIG. 10. Here, the mode for displaying the cleavage transition tree is changed for redrawing. At step 1001, it is determined whether the cleavage transition tree is currently displayed in the two-dimensional form or in the three-dimensional form. If it is in the two-dimensional, "three-dimensional" is stored as the cleavage transition tree display mode in a global variable at step 1002. If it is in the three-dimensional, "two-dimensional" (2D) is stored as the cleavage transition tree display mode in the global variable at step 1003. Then, the process for displaying the cleavage transition tree is called for KEEP at step 1004 and then the process returns to FIG. 7 through a connector 1005.

Figure 11:
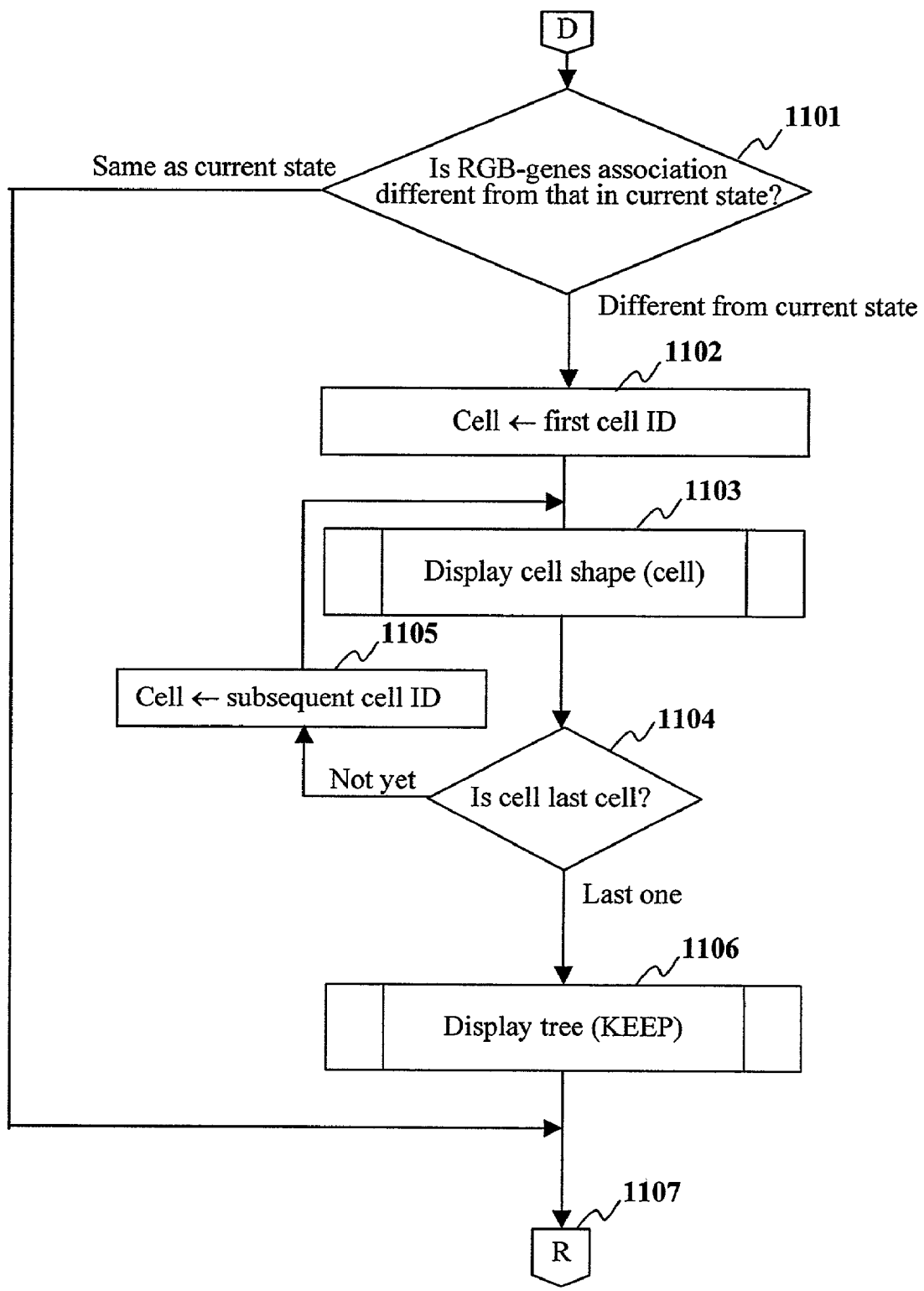
FIG. 11 is a flow chart illustrating details of a process for establishing association between RGB colors and genes.

Next, a process for establishing RGB-Gene association is described with reference to FIG. 11. Here, all cells are redrawn after three genes are assigned with colors R, G, or B. The cleavage transition tree is also redrawn during which it is colored. At step 1101, it is determined whether the association of R, G, and B with the genes is different from that in the current state. If it is same as that in the current state, then the process returns to FIG. 7 through a connector 1107. If it is different from that in the current state, a first cell ID is stored in a variable "CELL" at step 1102, which is used as an argument at step 1103 to call the process for displaying the cell shape. At step 1104, it is determined whether the "CELL" is the last cell to be processed. If it is not the last one, a subsequent cell ID is stored in the "CELL" at step 1105 and the process loops back to the step 1103. If it is the last cell, the process for displaying the cleavage transition tree is called for KEEP at step 1106. Then the process returns to FIG. 7 through the connector 1107 after the cleavage transition tree is redrawn.

Figure 12:
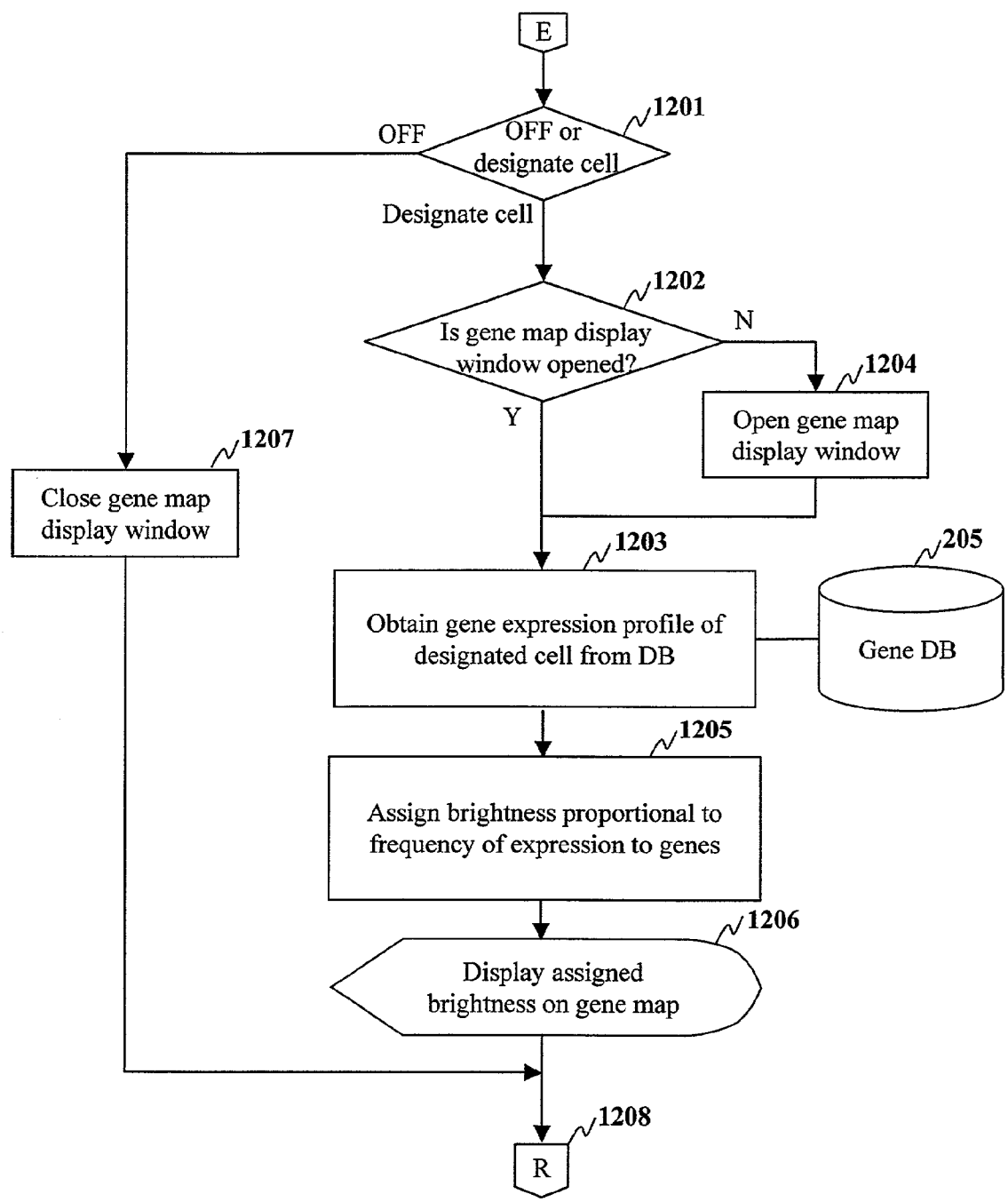
FIG. 12 is a flow chart illustrating details of a process for displaying a gene map.

Next, a process for displaying a gene map is described with reference to FIG. 12. Here, a gene is displayed on a gene map with a brightness proportional to the degree of expression, based on the expression profile of a designated cell.

First, at step 1201, it is determined whether the operation is to turn OFF or to designate a cell. If it is the OFF operation, then a gene map display window is closed at step 1207 and the process returns to FIG. 7 through a connector 1208. On the other hand, if the operation is to designate a cell, it is determined at step 1202 whether the gene map display window is opened. If it is not opened, the gene map display window is opened at step 1204. If it is opened already, a gene expression profile of the designated cell is obtained from the gene DB 205 at step 1203. At the following step 1205, brightness proportional to the frequency of expression is assigned to the genes that are displayed on the gene map at step 1206. The process then returns to FIG. 7 through the connector 1208.

Figure 13:
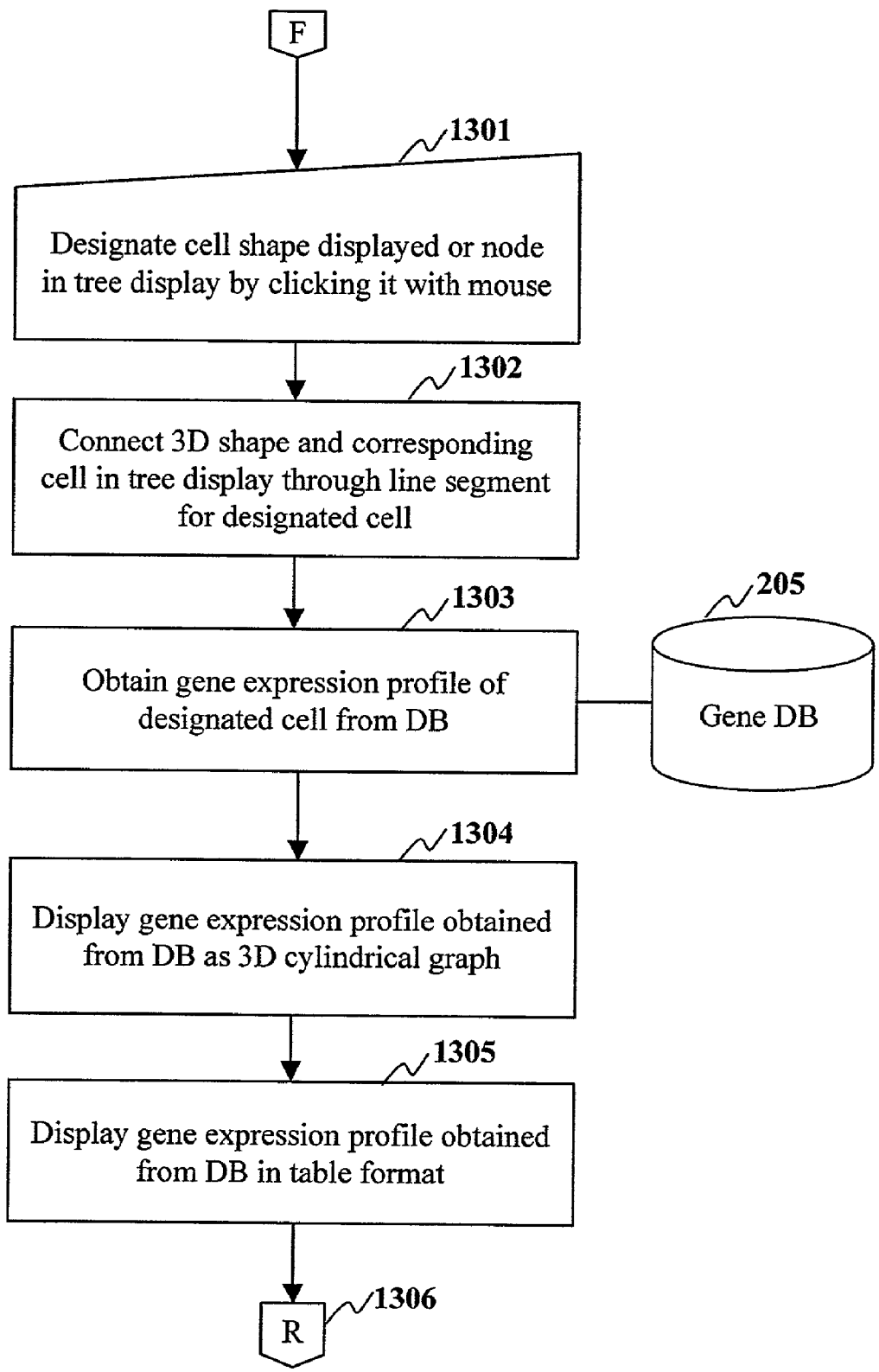
FIG. 13 is a flow chart illustrating details of a process for displaying an expression profile of a designated cell.

Next, a process for displaying an expression profile of a designated cell is described with reference to FIG. 13. Here, a cell is designated by means of clicking with a mouse a cell of a three-dimensional shape or a node in the cleavage transition tree and the expression profile of that cell is displayed.

First, at step 1301, a cell is designated with a mouse. At the following step 1302, the three-dimensional shape and the corresponding node in the cleavage transition tree is connected through a line segment for the selected cell. At step 1303, the expression profile of the designated cell is obtained from the gene DB 205. This expression profile is displayed as a three-dimensional cylindrical graph at step 1304. In addition, the same data is displayed in a table format at step 1305. The process then returns to FIG. 7 through a connector 1306.

Figure 14:
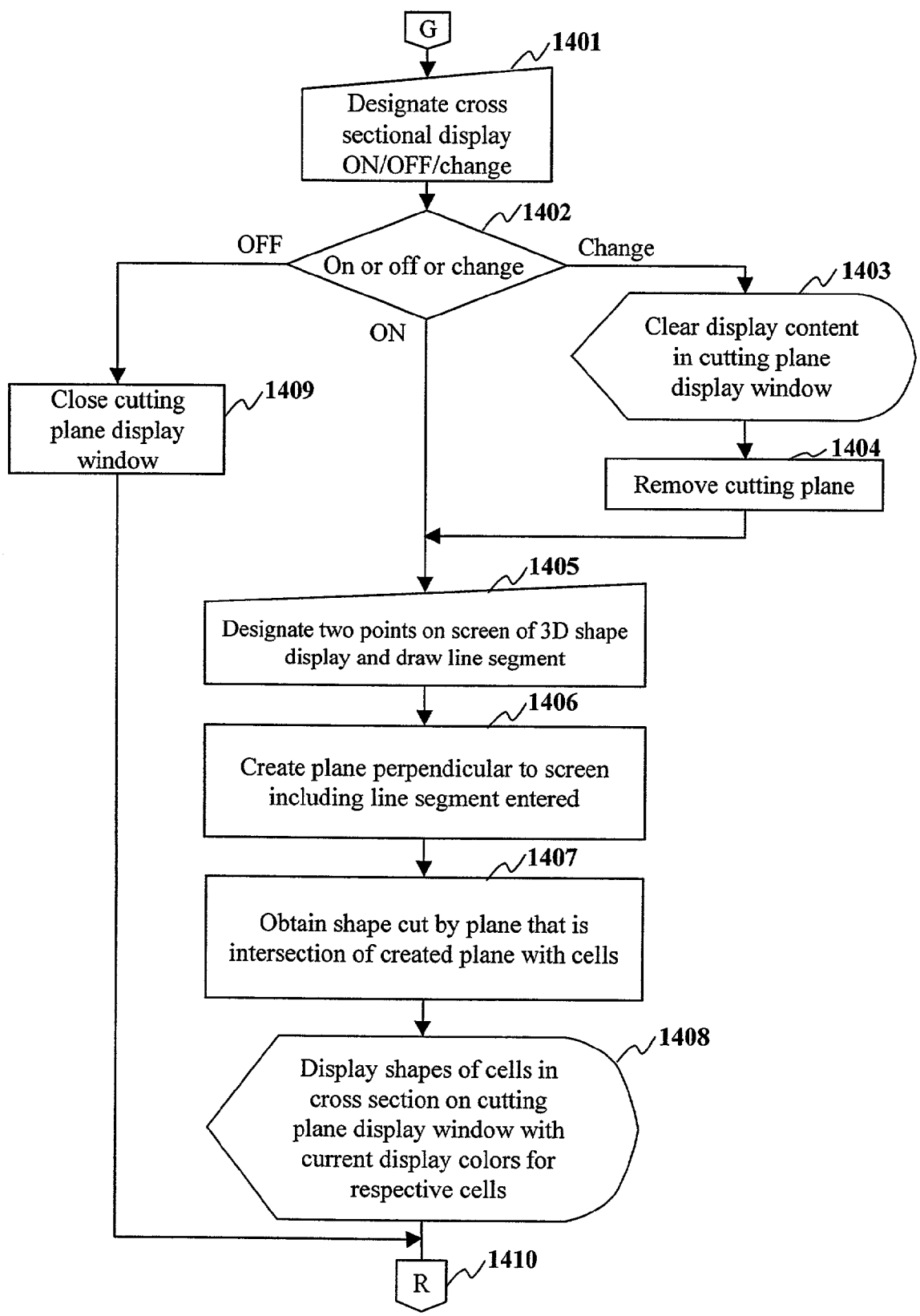
FIG. 14 is a flow chart illustrating details of a process for displaying a cross section at a designated cutting plane.

Next, a process for displaying an expression profile of a designated cell is described with reference to FIG. 14. Here, a cell having a three-dimensional shape is displayed in cross section. First, at step 1401, it is inquired whether presentation of a cross section is initiated (ON), terminated (OFF) or changed (CHANGE). At step 1402, it is determined. If the result indicates OFF, a cutting plane display window is closed at step 1409 and the process returns to FIG. 7 through a connector 1410.

If the result indicates CHANGE, the current display in the cutting plane display window is cleared at step 1403. The plane cutting the three-dimensional shape is removed at step 1404 to proceed to step 1405. If the result indicates ON, the process goes to the step 1405. Then, the observer designates two points on a screen with the view of the three-dimensional shape in order to designate a cutting plane and draws a line segment. At step 1406, a plane perpendicular to the screen is created, including the line segment. At step 1407, obtained is a shape cut by a plane that is the intersection of the cells with the created plane. At step 1408, the shapes of the cells in cross section are displayed on the cutting plane display window with the current display colors for the respective cells. The process then returns to FIG. 7 through the connector 1410.

Figure 15:
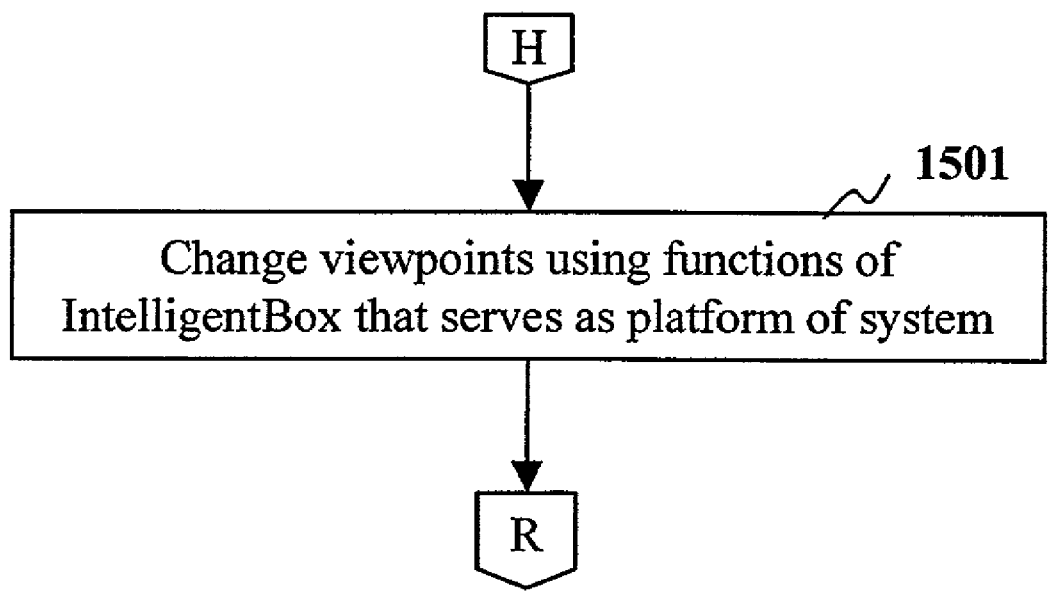
FIG. 15 is a flow chart illustrating details of a process for changing a viewpoint during display of a three-dimensional shape.

Next, a process for changing a viewpoint of a three-dimensional shape is described with reference to FIG. 15. The process for changing the viewpoints of the three-dimensional shapes (step 1501) completely relies on the functions of IntelligentBox that serves as the platform of the present embodiment. Accordingly, description thereof is omitted.

Figure 16:
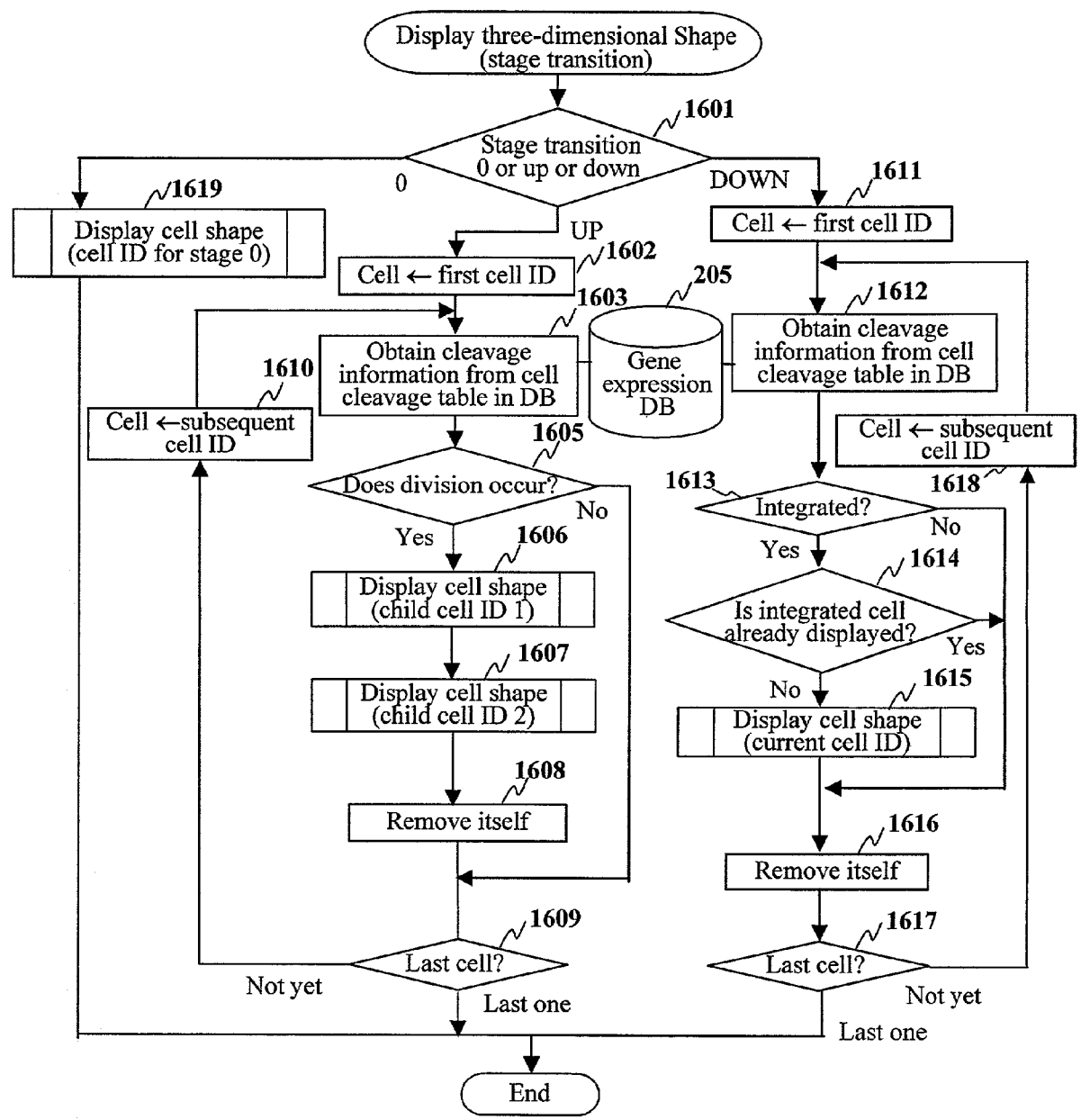
FIG. 16 is a flow chart illustrating details of a process for displaying a three-dimensional shape.

Next, a process for displaying the three-dimensional shape is described in detail with reference to FIG. 16. This process for displaying the three-dimensional shape is mainly called from the process illustrated as the flow chart in FIG. 8. The process for displaying the three-dimensional shape has a function to display "STAGE 0" which is the initial state and control UP/DOWN of the stages. A separate module processes drawing of the cells.

At step 1601, a stage transition used as an argument is checked. If it designates display of "STAGE 0", a process for displaying a cell shape is called at step 1619 with the cell ID for the "STAGE 0" used as the argument. Then, the process terminates.

If the step 1601 indicates UP, the cell ID of a first cell is stored in the variable "CELL" at step 1602. At step 1603, cleavage information is obtained from the cell cleavage table 302 in the gene DB 205 in which the cleavage information consists of the division stage 3022, the "CHILD CELL ID 1" 3023, and the "CHILD CELL ID 2" 3024, corresponding to the cell ID of the first cell. At the subsequent step 1605, it is determined whether the cell is divided as a result of this moving up the stage. If the division occurs, the process for displaying the cell shape is called for the two child cells (ID 1 and ID 2) at steps 1606 and 1607. At step 1608, the three-dimensional shape of itself (parent of the child cells) is removed to proceed to step 1609. It is noted that the data at the division stage 3022 in the cleavage table 302 in FIG. 3 indicates whether or not the cell division occurs at the subject stage.

If it is determined at the step 1605 that no division occurs, the process goes to the step 1609 where it is determined whether the cell under processing is the last cell to be processed. If it is not the last cell, then the cell ID of the subsequent cell is stored in the "CELL" variable at step 1610 and the process returns to the step 1603.

If the step 1601 indicates that the stage transition is DOWN, the cell ID of the first cell is stored in the variable "CELL" at step 1611. At step 1612, cleavage information is obtained from the cell cleavage table 302 in the gene expression DB 205 in which the cleavage information consists of the "DIVISION STAGE" 3022, the "CHILD CELL ID 1" 3023, and the "CHILD CELL ID 2" 3024, corresponding to the cell ID of the first cell. At the subsequent step 1613, it is determined whether the cell is integrated as a result of moving down the stage. It is noted that the data at the division stage 3022 in the cleavage table 302 in FIG. 3 indicates whether or not the integration occurs. If integrated, it is determined at step 1614 whether the parent cell is already displayed by a sibling cell. If not displayed, the process for displaying the cell shape is called at step 1615 with the cell ID of the parent cell used as the argument and the process goes to step 1616.

If the step 1613 indicates that no integration occurs, the process goes to step 1617. If it is found at the step 1614 that the parent cell is already displayed, the display of the three-dimensional shape of itself (child cell) is removed at the step 1616. Thereafter, the step 1617 is carried out where it is determined whether the cell under processing is the last cell to be processed. If it is not the last cell, then the cell ID of the subsequent cell is stored in the "CELL" variable at step 1618 and the process returns to the step 1612.

If it is found at the steps 1609 and 1617 that the cell is the last one, then the process terminates.

Next, a process for displaying a cleavage transition tree is described with reference to FIGS. 17 to 20. The major functions of the module of the cleavage transition tree are the following four functions. The recursive algorithm is used within the module that is suitable for the cleavage transition tree.

(1) To display the root of the cleavage transition tree.

(2) To move up one level of the display stage in the cleavage transition tree.

(3) To move down one level of the display stage in the cleavage transition tree.

(4) To redraw the cleavage transition tree when color display of the expression profile is designated or when the mode (3D/2D) of displaying the cleavage transition tree is changed.

Figure 17:
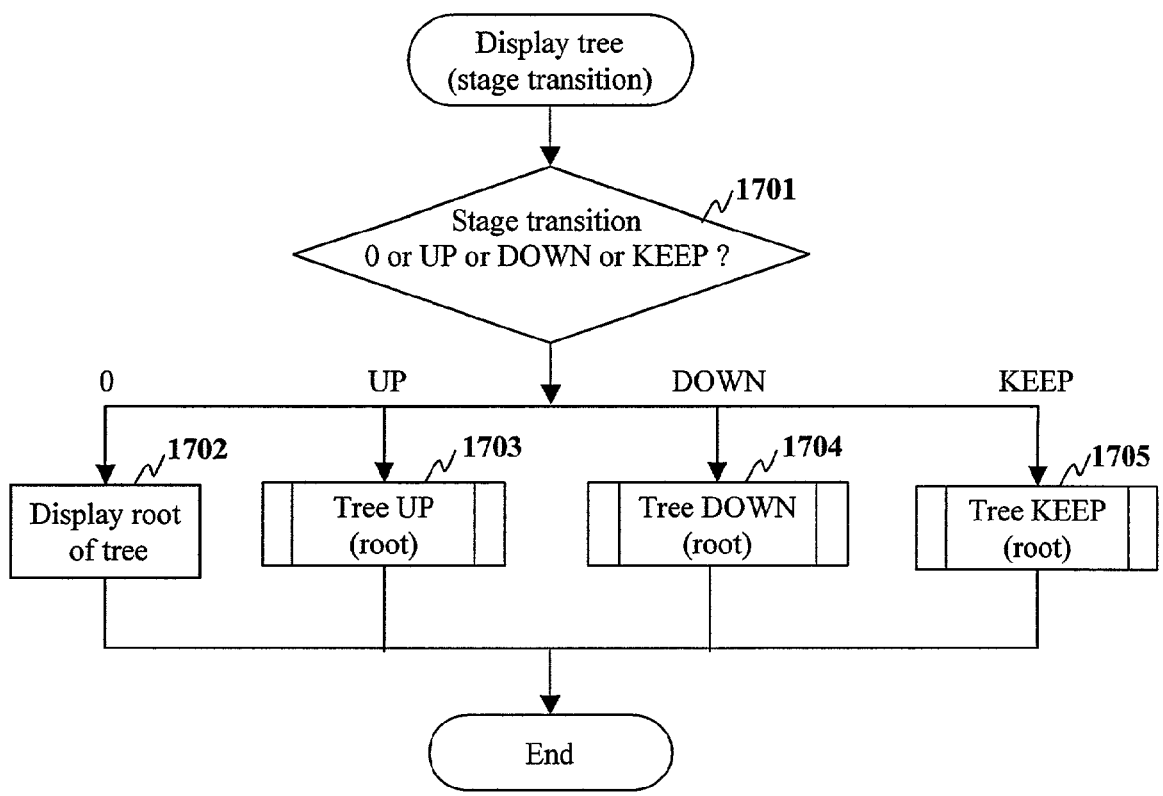
FIG. 17 is a flow chart illustrating details of a process for displaying a cleavage transition tree.

First, one of the above-mentioned four functions is selected at step 1701 in FIG. 17. When the stage transition used as the argument indicates "0", the root of the cleavage transition tree is displayed at step 1702. When the stage transition used as the argument indicates "UP", the process for moving UP in the cleavage transition tree is called at step 1703 with the root of the cleavage transition tree used as the argument in order to move up one level of the display stage in the cleavage transition tree. When the stage transition used as the argument indicates "DOWN", the process for moving DOWN in the cleavage transition tree is called at step 1704 with the root of the cleavage transition tree used as the argument in order to move down one level of the display stage in the cleavage transition tree. When the stage transition used as the argument indicates "KEEP", the process to KEEP the cleavage transition tree is called at step 1705 with the root of the cleavage transition tree used as the argument in order to redraw the cleavage transition tree.

Figure 18:
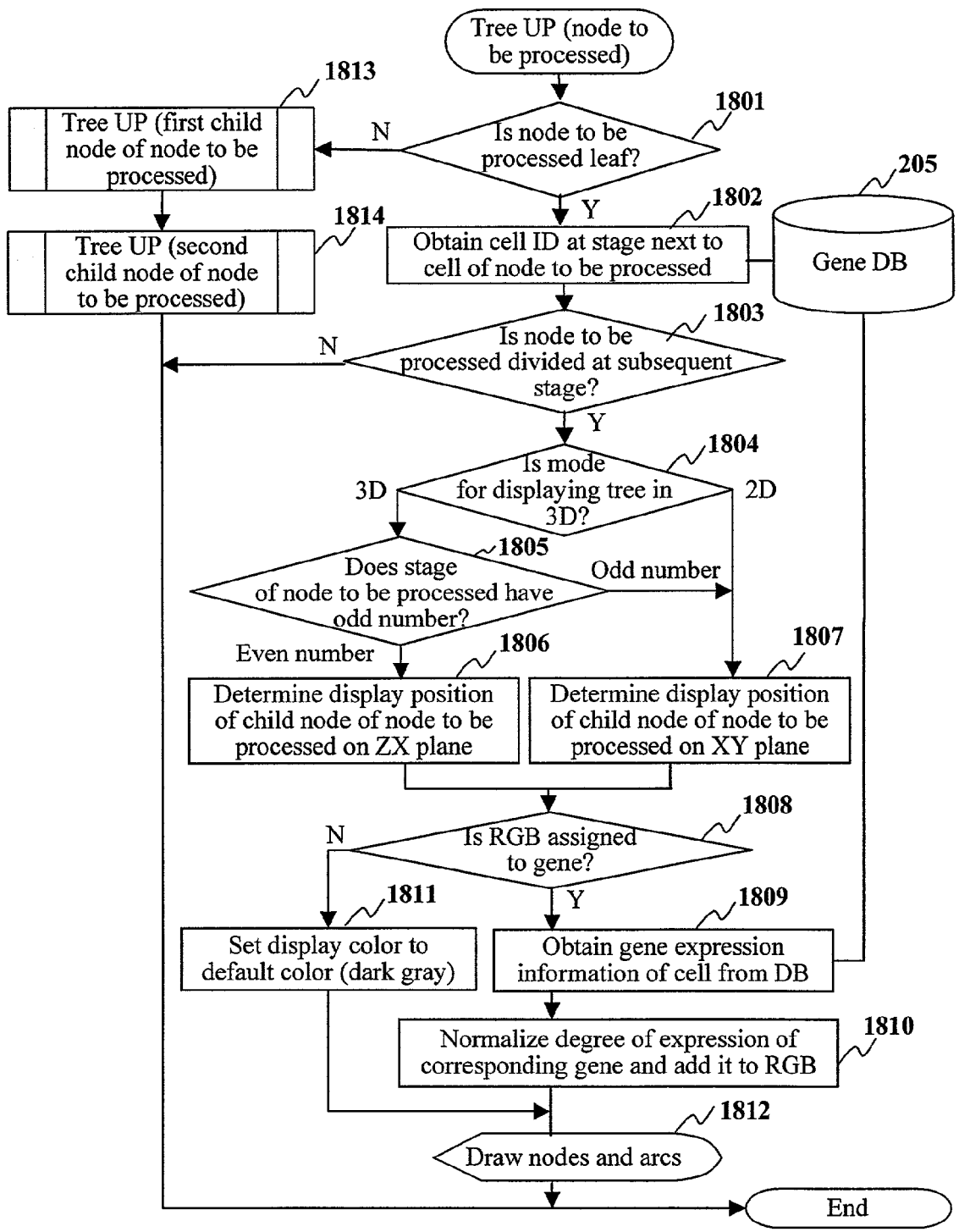
FIG. 18 is a flow chart illustrating a process for moving UP through stages in a cleavage transition tree as the process for displaying the cleavage transition tree.

Next, the process for moving UP through stages in the cleavage transition tree as the process for displaying the cleavage transition tree is described with reference to FIG. 18. The process for moving UP in the cleavage transition tree is achieved as a recursive module that receives a node of the cleavage transition tree as the argument, moves up the stage by creating a child node when the received one is a "leaf node", and calls itself with the "child node" of its own used as the argument when the received one is not a "leaf node". Whether or not the node is a "leaf node" is determined based on whether or not the subject node has a child. If a node has no child, it is a leaf node.

Details are described below.

At step 1801, it is determined whether the argument, that is, the node to be processed is a "leaf node". If it is not a "leaf node", the process calls itself (the process for moving UP in the cleavage transition tree) recursively with the "child node" of the node to be processed being used as the argument at steps 1813 and 1814. Then, the process terminates.

When it is found at the step 1801 that the argument, that is, the node to be processed is a "leaf", then step 1802 is carried out where the ID of the child cell at the subsequent stage is obtained from the gene DB 205. At step 1803, it is determined whether the cell of the node to be processed is divided at the subsequent stage. If it is not divided, the process is terminated without any operation. If it is divided, step 1840 is carried out. At the step 1804, it is determined whether the mode for displaying the cleavage transition tree is in two-dimensional or three-dimensional. If it is in two-dimensional, display coordinates of the child node of the node to be processed are defined on an XY plane. If it is in three-dimensional, it is determined whether the display position of the child node is displayed on the XY plane (step 1807) or is displayed on an ZX plane (step 1806), depending on whether the stage of the node to be processed has an odd number or an even number (step 1805). Then, coordinates are calculated.

Next, for the drawing, color should be used when the colors R, G, and B are assigned to the genes. At step 1808, it is determined whether R, G, and B are assigned to the genes. If they are not assigned, the drawing color is set as a default dark gray (step 1811). If it is assigned, the expression information is obtained from the gene expression profile table 301 in the gene DB 205 at step 1809. The data is normalized at step 1810 and is added to R, G, and B, thereby determining the display colors. The normalization is required to limit the values of the R, G, and B within a range of from 0 to 256.

The subsequent step 1812 draws the nodes and arcs (line segments connecting between the nodes) according to the result of the above-mentioned processes.

Figure 19:
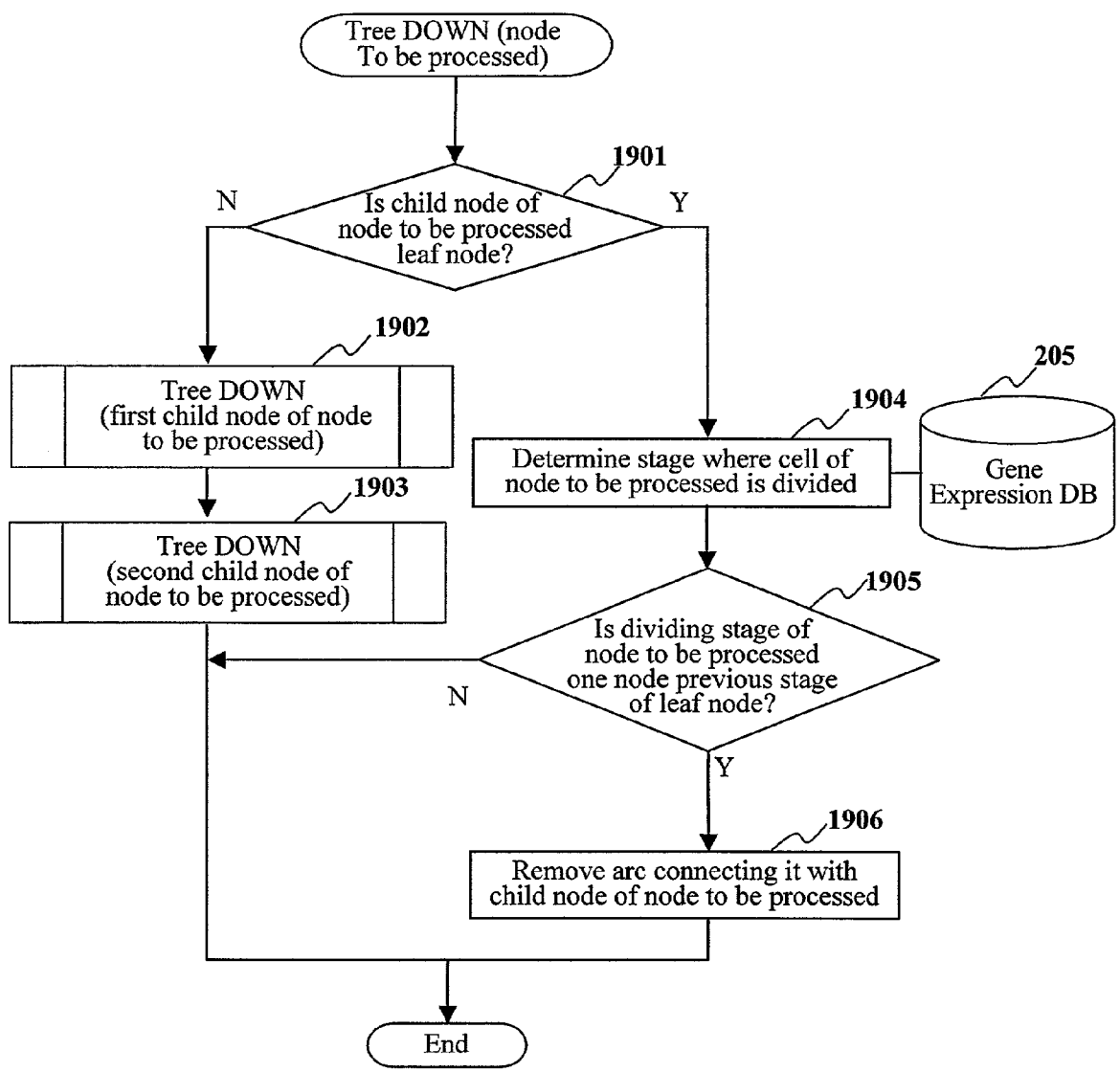
FIG. 19 is a flow chart illustrating a process for moving DOWN through stages in a cleavage transition tree as the process for displaying the cleavage transition tree.

Next, the process for moving DOWN through stages in the cleavage transition tree as the process for displaying the cleavage transition tree is described with reference to FIG. 19.

The process for moving DOWN in the cleavage transition tree is achieved as a recursive module that receives a node of the cleavage transition tree as the argument, moves down the stage by removing a child node when the received one is a parent of a leaf node, and calls itself with the child node of its own used as the argument when the received one is not the parent of a leaf node. Whether or not the node is the parent of a leaf node is determined based on whether or not the child node of its own is a leaf node. Details are described below.

At step 1901, it is determined whether the argument, that is, the child node of the node to be processed is a "leaf node". If it is not a "leaf node", the process calls itself recursively with the child node of the node to be processed being used as the argument at steps 1902 and 1903. Whether or not the child node is a leaf node can be determined based on whether or not the child node has a child.

When it is found at the step 1901 that the child node of the node to be processed is a leaf node, then step 1904 is carried out where the information 3022 about the stage where the cell of the node to be processed is divided is obtained by means of accessing the cleavage table 302 in the gene DB 205. At step 1905, it is determined whether the dividing stage of the node to be processed is one node previous to the stage of the leaf node. In other words, it is determined whether or not it is required to remove the leaf during the operation to move down through the stages in the cleavage transition tree. If it is required, the arc connecting the node to be processed with its child node is removed at step 1906. If not, the process terminates without any operation.

Figure 20:
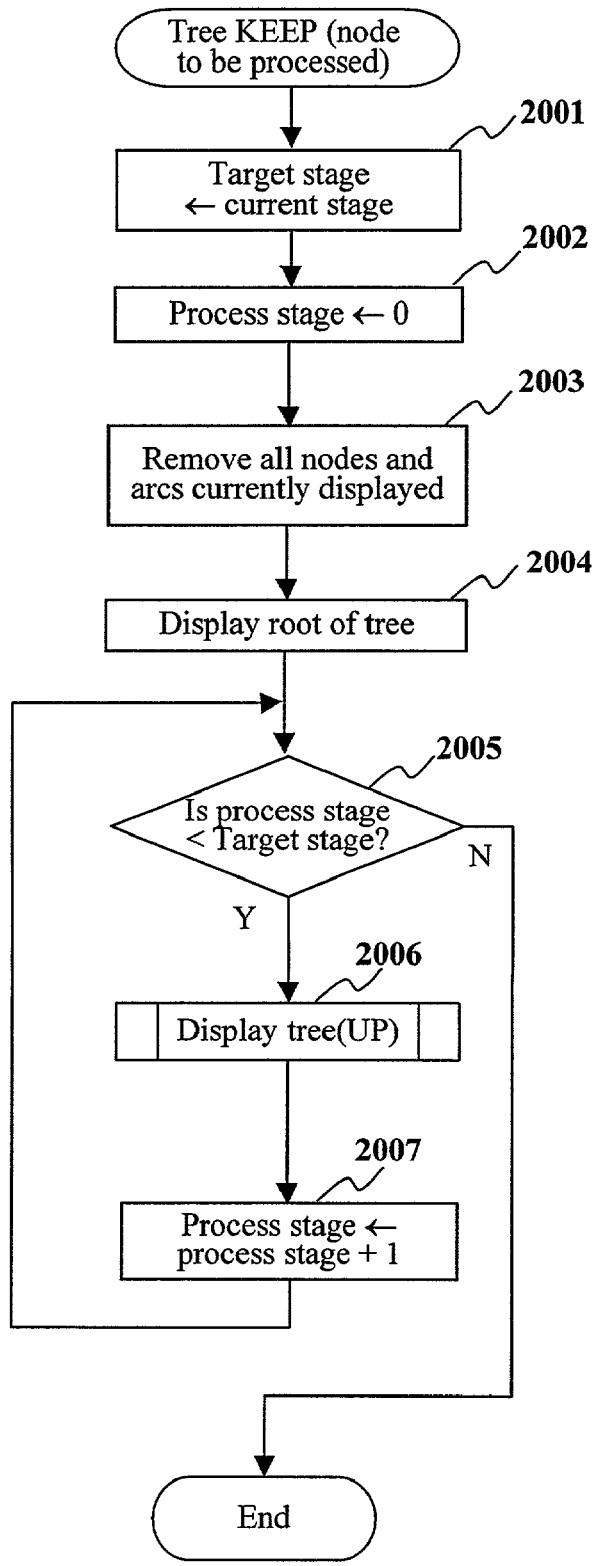
FIG. 20 is a flow chart illustrating a process to KEEP a cleavage transition tree for redrawing the cleavage transition tree as the process for displaying the cleavage transition tree.

Next, the process to KEEP the cleavage transition tree to redraw the cleavage transition tree as the process for displaying the cleavage transition tree is described with reference to FIG. 20.

The process to KEEP the cleavage transition tree is achieved by means of iteration of receiving a node of the cleavage transition tree as the argument, removing the cleavage transition tree currently displayed, and then calling the process for displaying the cleavage transition tree for UP to redraw to the current stage. Details are described below.

At step 2001, the current stage is kept aside as the target stage. At step 2002, "0" is assigned to the work variable "PROCESS STAGE". At step 2003, the current nodes and arcs displayed are all removed. At step 2004, the root of the cleavage transition tree is redrawn. Next, at step 2005, the process stage is compared with the target stage. If the process stage does not reach the target stage, then step 2006 calls the process for displaying the three-dimensional shape for UP. Step 2007 increments (+1) the work variable "PROCESS STAGE" and the process loops back to the step 2005. The process terminates when the step 2005 indicates that the target stage is reached.

Figure 21:
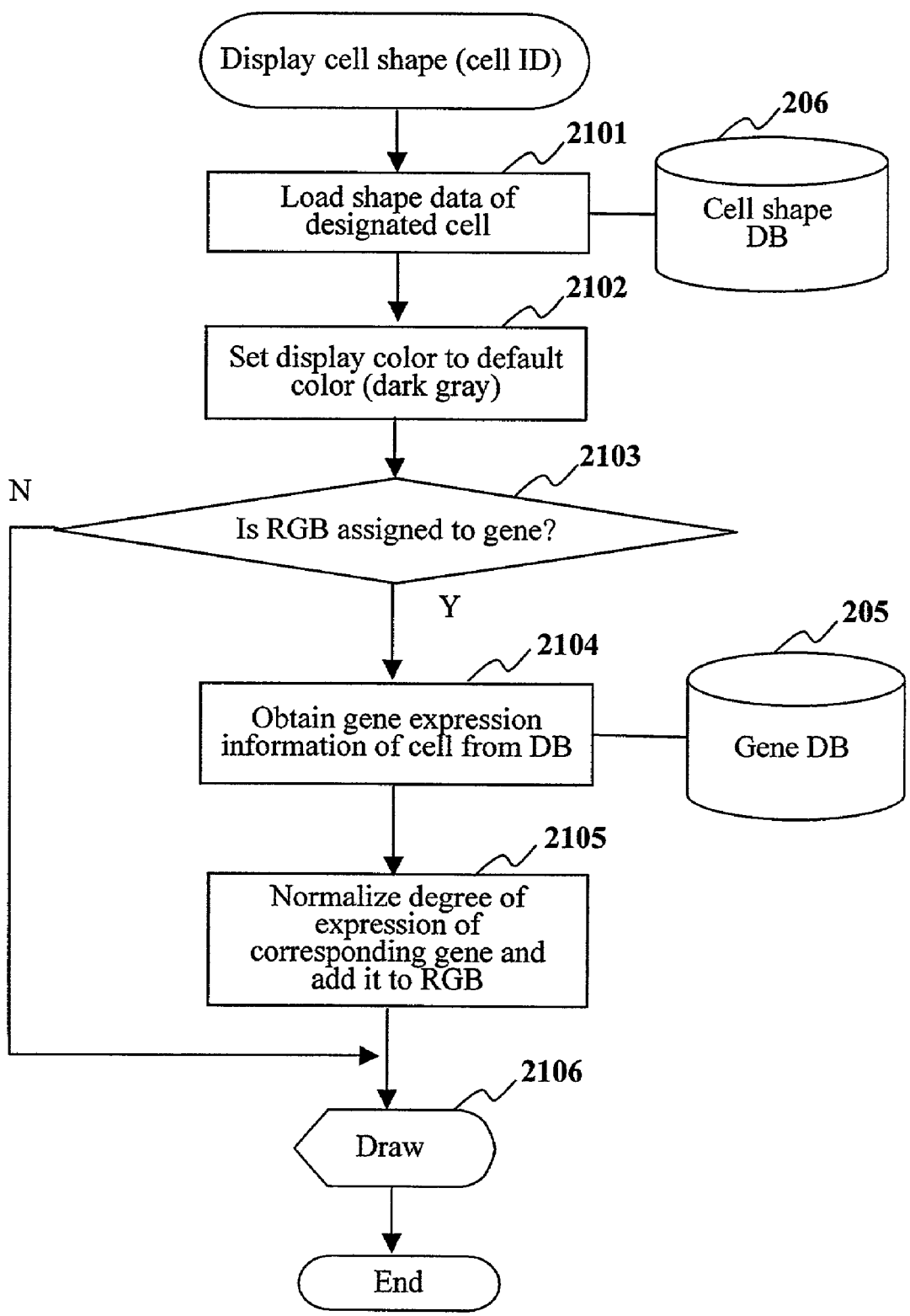
FIG. 21 is a flow chart illustrating a process of a module for displaying a cell shape.
Figure 22:
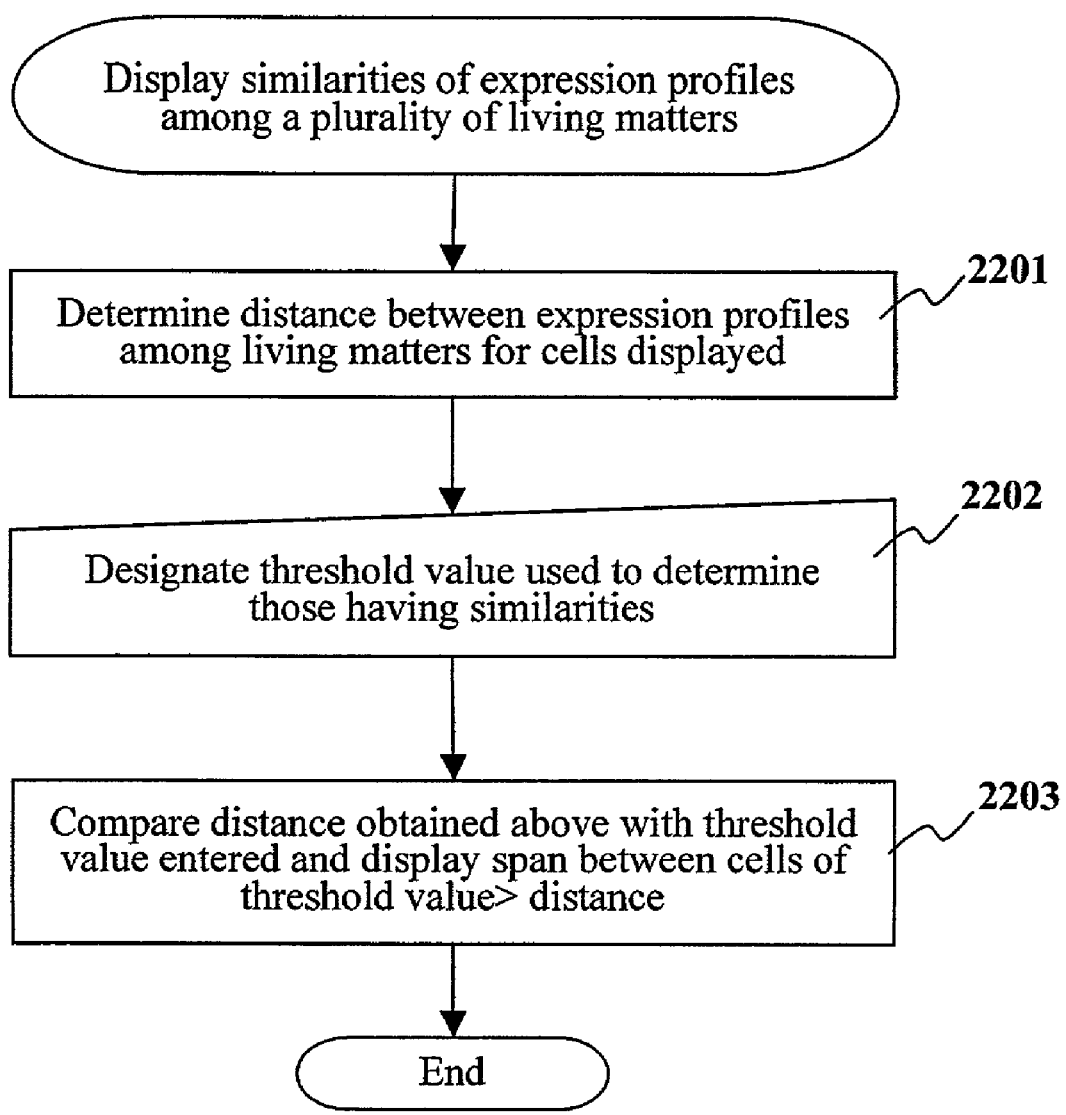
FIG. 22 is a flow chart illustrating a process for use in observing similarities in development of a plurality of living matters.

Next, described with reference to FIG. 21 is the process for displaying the cell shape that is mainly called from the module of the process for displaying the three-dimensional shape shown in FIG. 16. The module of the process for displaying the cell shape receives, as the name implies, a cell ID as the argument to draw the shape of the cell.

At step 2101, the data indicative of the cell shape used for the argument is obtained from the cell shape DB 206. Next, at step 2102, the display color is changed to the default dark gray. At step 2013, it is determined whether R, G, and B are assigned to the genes. If they are not assigned to, step 2106 is carried out for redrawing. Then the process terminates. If R, G, and B are assigned to, the expression profile about the cell used as the argument is obtained from the gene profile table 301 in the gene DB 205 at step 2104. Step 2105 normalizes the degree of expression of the subject gene, which is added to R, G, and B to determine the display colors. Then, step 2106 is carried out for redrawing and the process terminates.

Next, described is a function for use in observing similarities in development of a plurality of living matters. This is a function of activating a plurality of "the processes for displaying a subject (organism)" described in conjunction with FIG. 7 by the process in FIG. 6 to compare the expression profiles with each other and connect the cells having similar expression profiles through line segments.

First, at step 2201, a distance between expression profiles are obtained among the living matters for the cells displayed.

At step 2202, a threshold value is designated that is used to determine the cells having similarities to be connected through a line segment. At step 2203, the distance obtained above is compared with the threshold value to display the length of "threshold value>distance" with connections.

In the above-mentioned embodiment, description has been made in conjunction with such function that the similarities of the expression profiles are indicated with colors for up to three genes by means of assigning the degree of expression to R, G, and B. A method for extending this for four or more genes is described below with reference to FIG. 23.

Figure 23A:
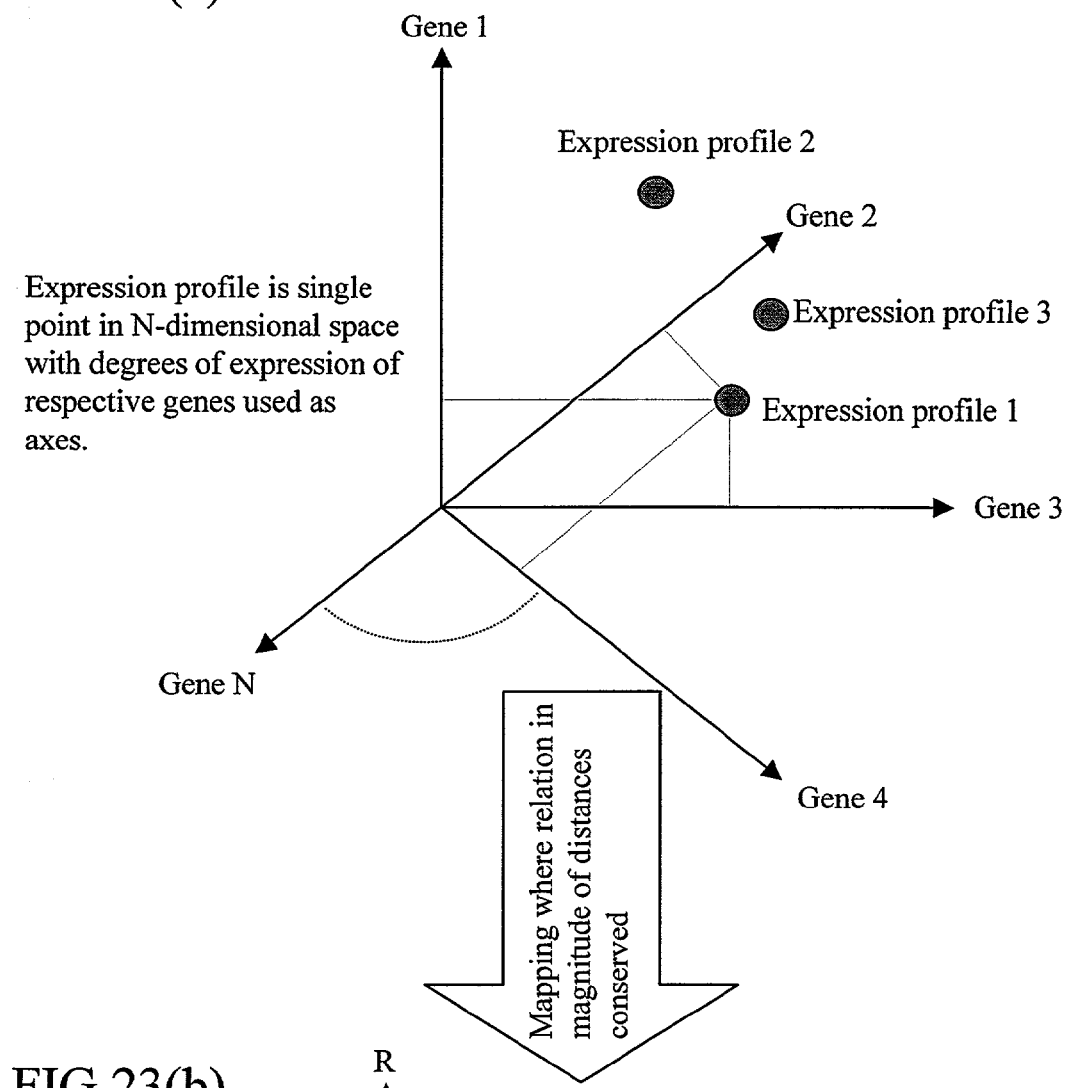
FIG. 23 is a view for use in describing a function to represent, with colors, similarities of expression profiles for four or more genes.
Figure 23B:
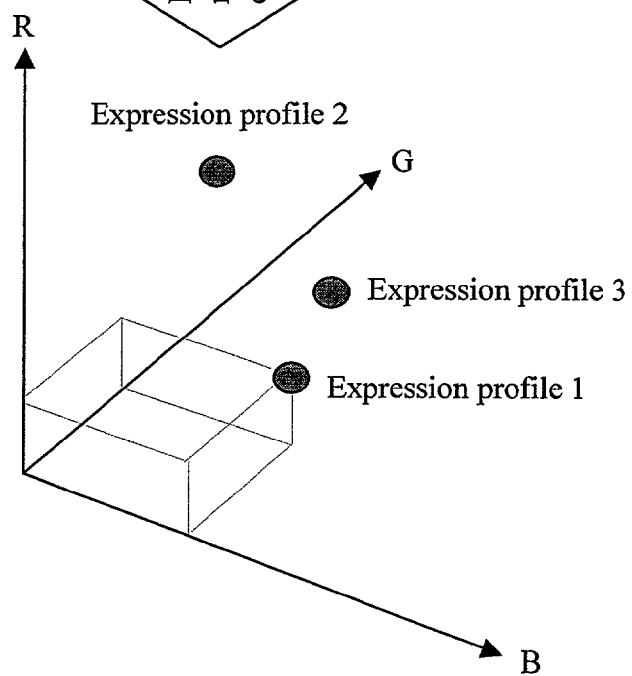

The expression profile is a vector formed of a combination of degrees of expression of which number is equal to that of genes, as shown in FIG. 23(*a*). Let the number of the genes be N, the expression profile may be expressed as a single point in an N-dimensional space. On the other hand, the color space is a three-dimensional space as a combination of the brightness of the three primary colors, R, G, and B. Color may be represented as a single point in that space. A requirement that should be satisfied is to represent the expression profiles of larger similarities using colors of larger similarities. This means that, as shown in FIG. 23(*b*), the expression profiles that are close to each other in the N-dimensional space should be assigned (mapped) such that they are also close in the color space and those that are away from each other should be assigned farther.

Algorithms to map a point in the N-dimensional space to a three-dimensional space include a known spring model.

Figure 24:
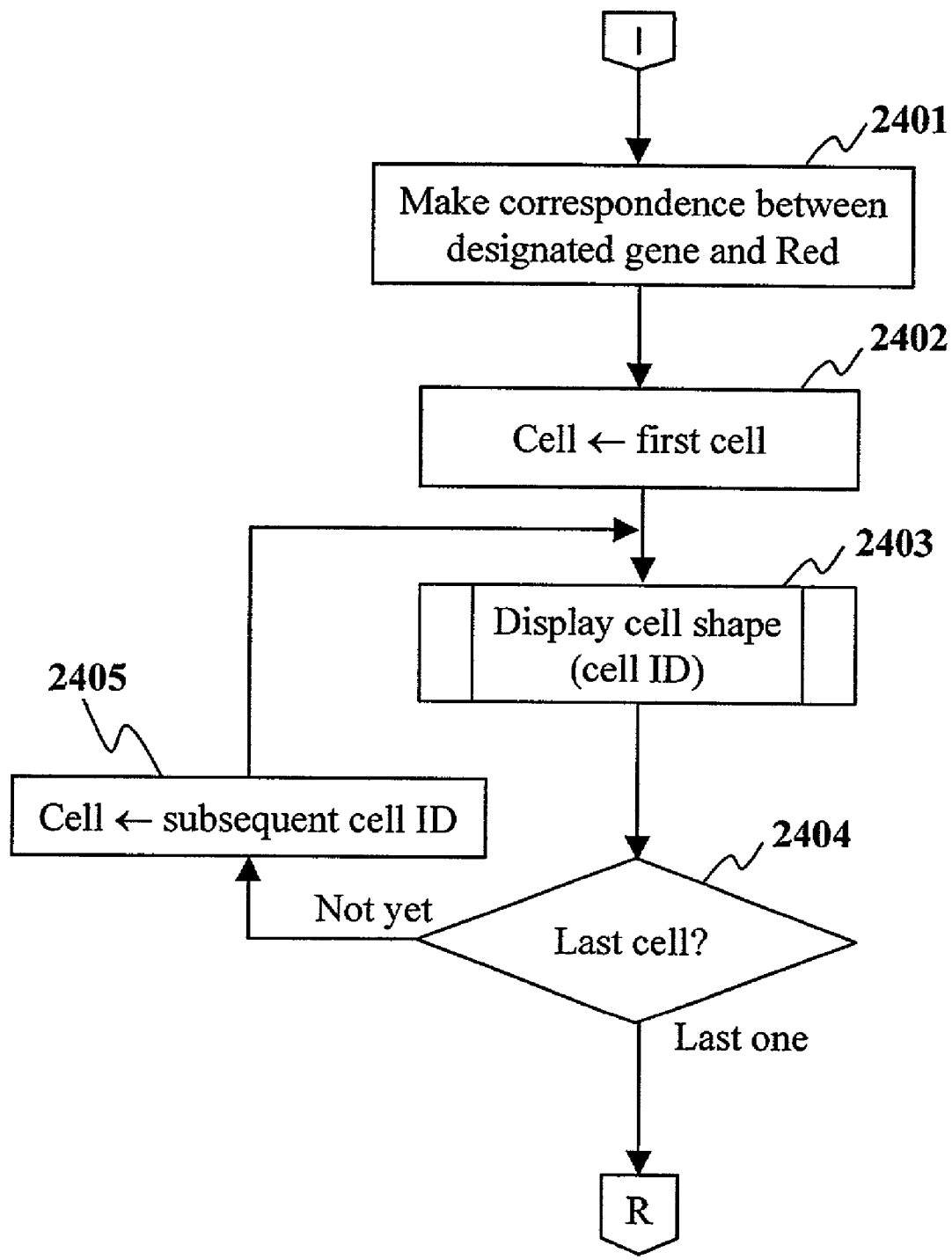
FIG. 24 is a flow chart illustrating a process for coordinating and displaying in a predetermined display format three-dimensional images representing expression phenomena of genes in two or more cells or sites and positions of genes on a gene map that cause expression.

FIG. 24 is a flow chart illustrating a process for coordinating and displaying in a predetermined display format three-dimensional images representing expression phenomena of genes in two or more cells or sites and positions of genes on a gene map that cause expression.

Here, a cell or a site containing the gene designated on the gene map is colored at a depth depending on the degree of the expression of that gene. At step 2401, Red is assigned to a designated gene in RGB-gene association. At step 2402, the first cell ID is stored in the variable "CELL". At step 2403, the process for displaying the cell shape is activated for that cell. As a result, the cell or the site containing the designated gene is colored red at a depth depending on the degree of the expression of that gene. At step 2404, it is determined whether the cell currently processed is the last cell. If it is not the last cell, the subsequent cell ID is stored in the "CELL" variable at step 2405. Then, the process loops back to the step 2403.

Figure 25:
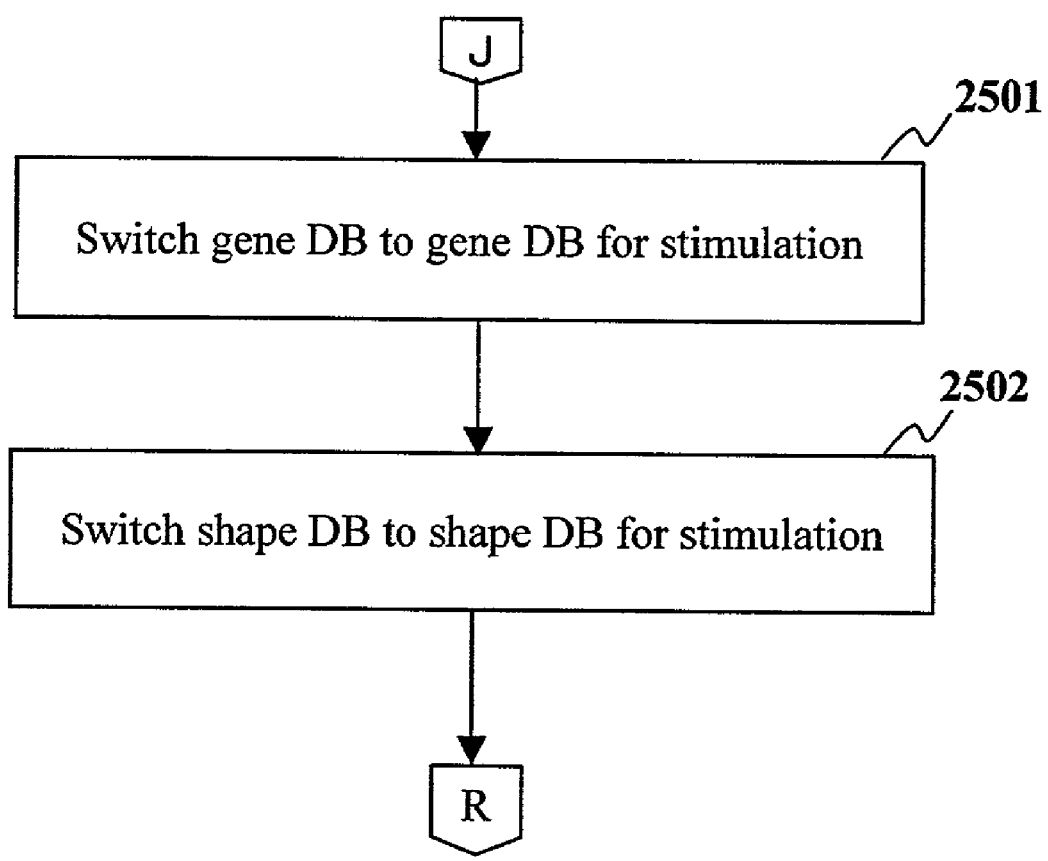
FIG. 25 is a flow chart illustrating a process for coordinating and displaying in a predetermined display format three-dimensional images representing expression phenomena of genes in two or more cells or sites and positions of genes on a gene map that cause expression.

FIG. 25 is a flow chart illustrating in summary a process for displaying chronologically a change in shape of the cell or the site caused by an external stimulation or a change in shape of the cell or the site caused by the living activities of its own and displaying a change of the three-dimensional image representing the expression phenomenon as an animation from a certain viewpoint at a certain instant of time.

Here, the gene DB is switched to a gene DB for stimulation (step 2501), then the cell shape DB is switched to a cell shape DB for stimulation (step 2502).

Therefore, it is possible to display as the animation the change in shape of the cell or the site caused by an external stimulation and the change of the three-dimensional image representing the expression phenomenon by means of preparing separately the gene DB for stimulation and the cell shape DB for stimulation.

Figure 26:
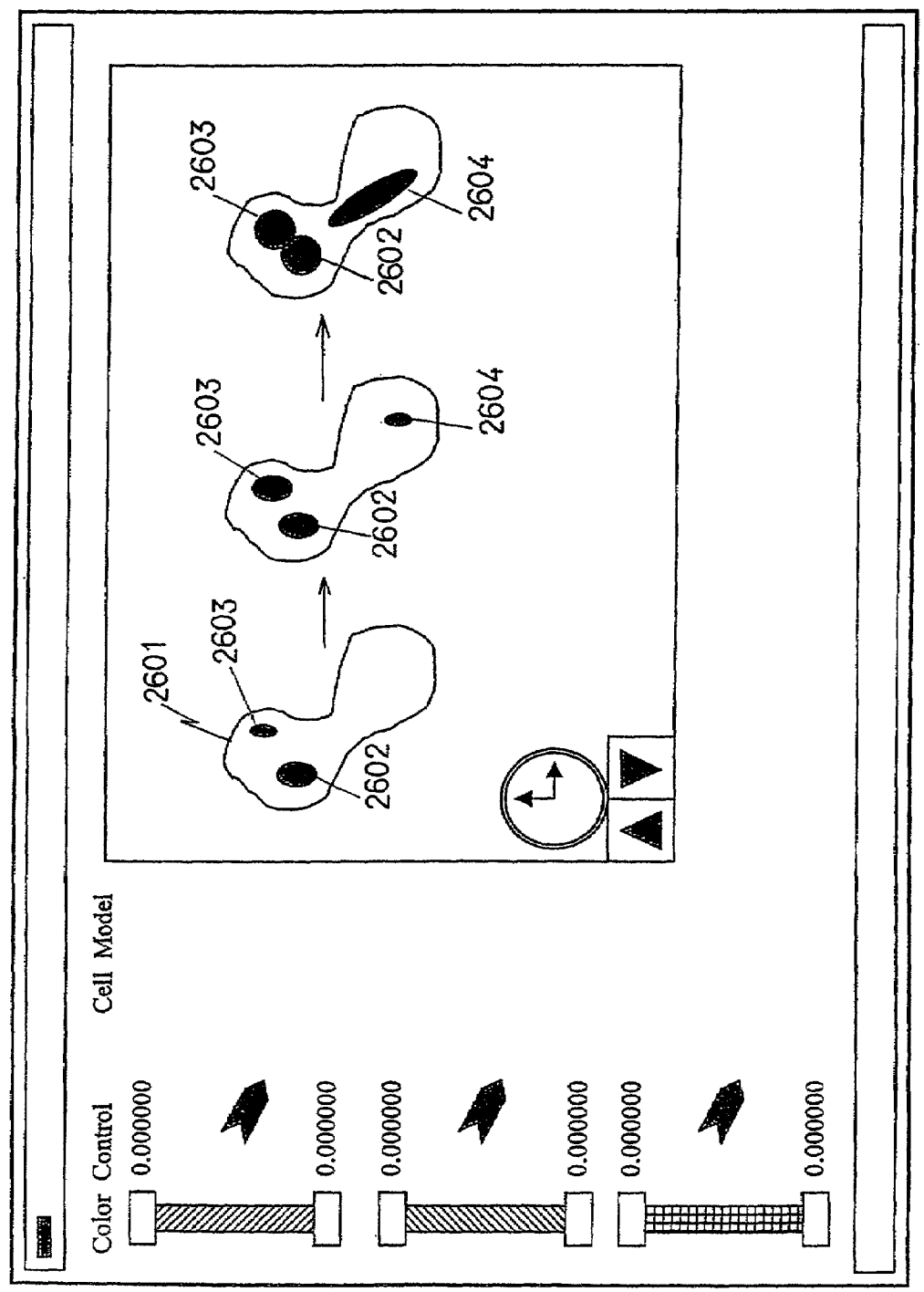
FIG. 26 is a view showing an example of three-dimensional images representing expression phenomena of genes at a site in a living matter, in which the images are created at a set viewpoint or at a fixed viewpoint and are displayed in one color or multiple colors in various scales depending on a frequency of expression of the gene in the subject site.

FIG. 26 is a view showing an example of three-dimensional images representing expression phenomena of genes at the site in the living matter, in which the images are created at a set viewpoint or at a fixed viewpoint and are displayed in one color or multiple colors in various scales depending on the frequency of expression of the gene in the subject site. Here, illustrated is an example where the change in frequency of expression in sites 2601 to 2604 of a living matter 2601 is displayed along the time axis.

Figure 27:
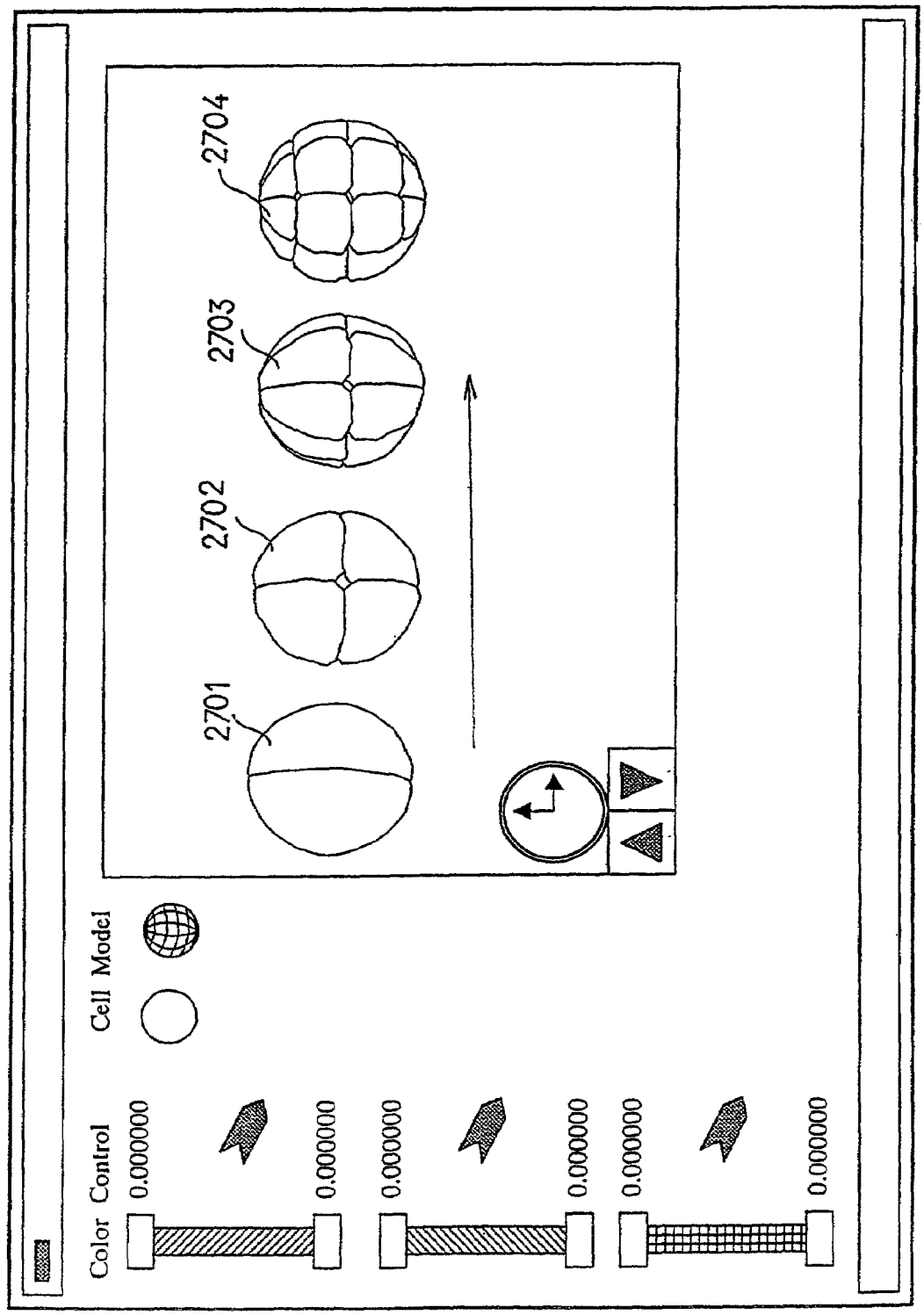
FIG. 27 is a view showing an example in which a change in shape of a cell (or a site) associated with embryogenesis of gene expression is chronologically displayed and a change of a three-dimensional image representing an expression phenomenon is displayed as an animation from a certain viewpoint at a certain instant of time.

FIG. 27 is a view showing an example in which a change in shape of the cell (or the site) associated with embryogenesis of gene expression is chronologically displayed and a change of the three-dimensional image representing the expression phenomenon is displayed as an animation from a certain viewpoint at a certain instant of time. Here, the change from two cells to sixteen cells is displayed as an animation along the time axis. A rate of change for the animation display may be determined arbitrarily.

Figure 28:
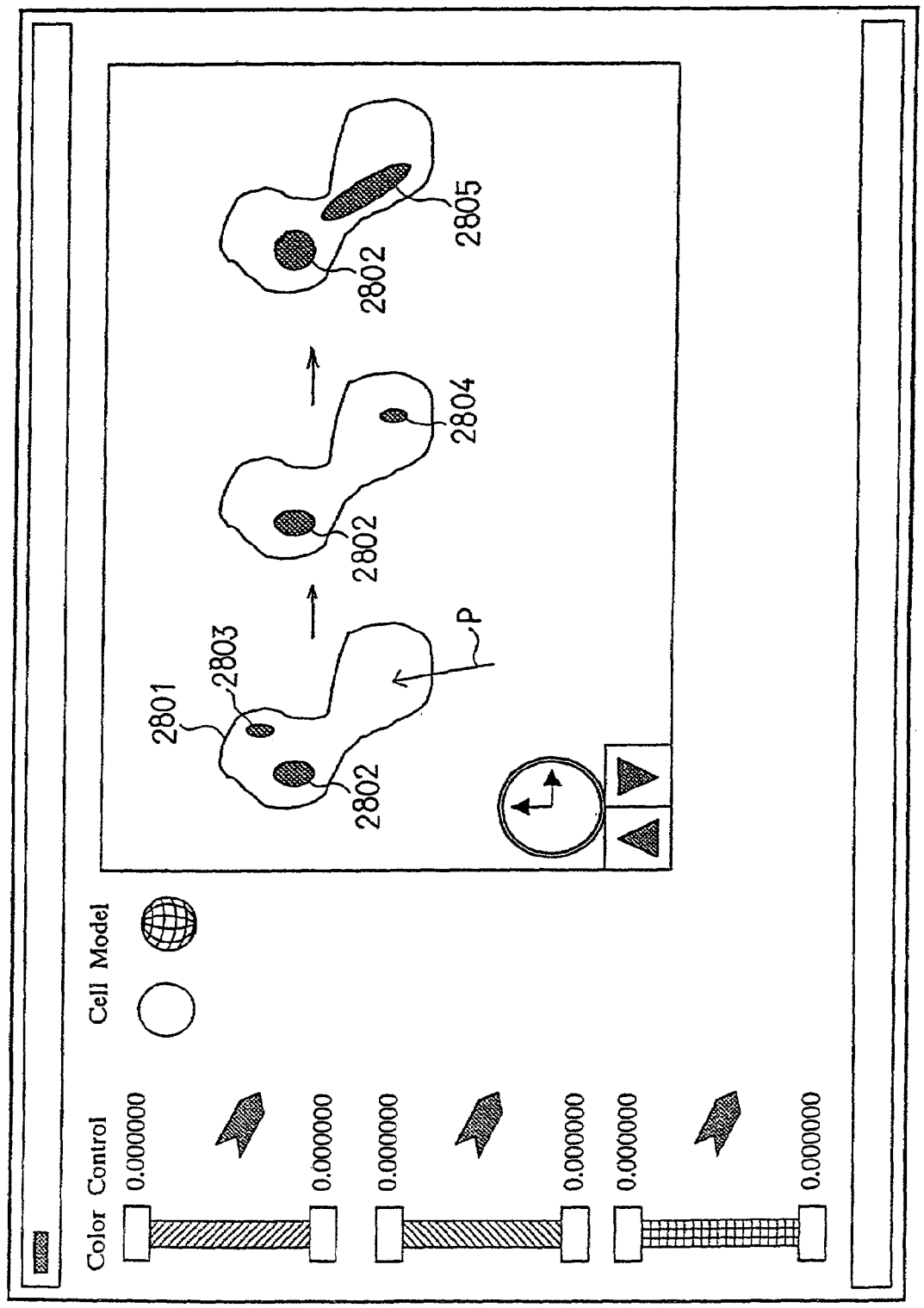
FIG. 28 is a view showing an example in which a change in shape of a cell or a site of the living matter caused by an external stimulation or a change in shape of a cell or a site caused by the living activities of its own is chronologically displayed, and a change of a three-dimensional image representing an expression phenomenon is displayed as an animation from a certain viewpoint at a certain instant of time.

FIG. 28 is a view showing an example in which a change in shape of the cell or the site of the living matter caused by the external stimulation or a change in shape of the cell or the site caused by the living activities of its own is chronologically displayed and a change of a three-dimensional image representing an expression phenomenon is displayed as an animation from a certain viewpoint at a certain instant of time. Here, the change in shapes of sites 2802, 2803, 2804, and 2805 is displayed along the time axis when the external simulation is applied to a living matter 2801 at the position designated by an arrow P.

Figure 29:
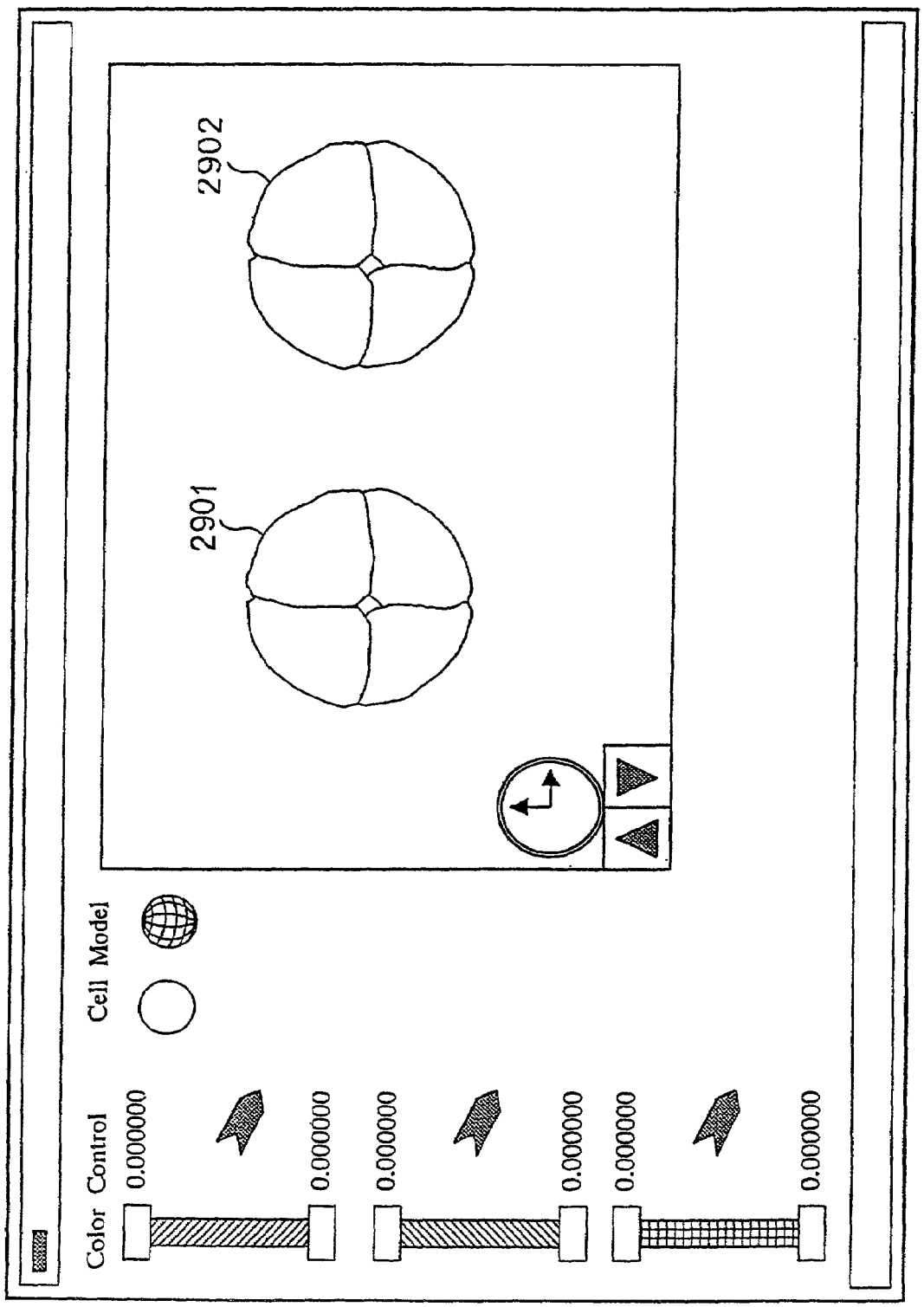
FIG. 29 is a view showing an example in which three-dimensional images representing expression phenomena for each cell or site of two or more living matters are displayed in parallel.

FIG. 29 is a view showing an example in which the three-dimensional images representing the expression phenomena for each cell or site of two or more living matters are displayed in parallel. Here, illustrated is an example in which the three-dimensional images representing the expression phenomena of the cells of two living matters 2901 and 2902 are displayed in parallel.

Figure 30:
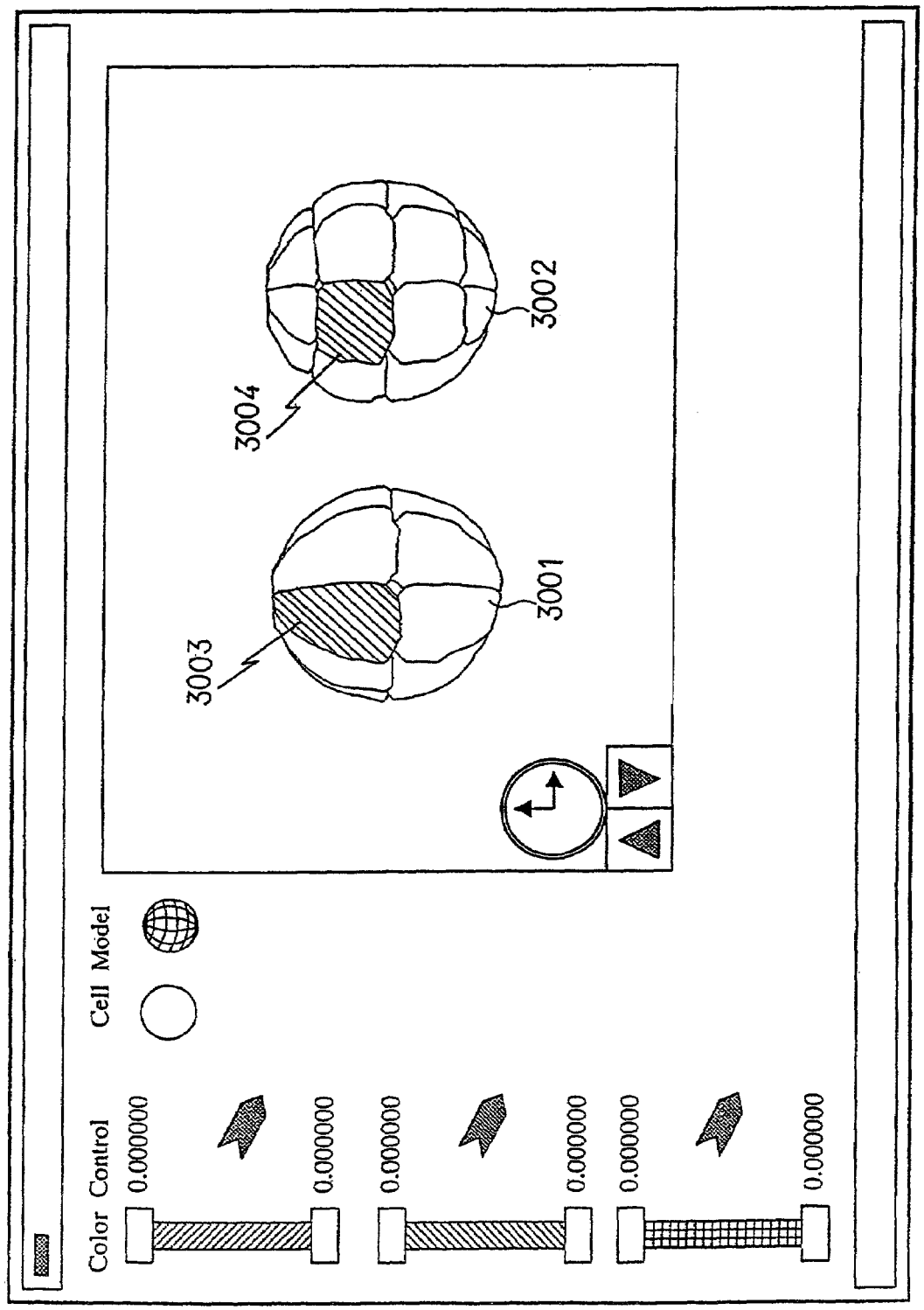
FIG. 30 is a view showing an example in which three-dimensional images representing expression phenomena for each cell or site of two or more living matters are compared and similarities therebetween are visually displayed in a predetermined display format.

FIG. 30 is a view showing an example in which three-dimensional images representing expression phenomena for each cell or site of two or more living matters are compared and similarities therebetween are visually displayed in a predetermined display format. Here, the fact that sites represented by reference numerals 3003 and 3004 in two living matters 3001 and 3002 are similar to each other is displayed with the same color.

Figure 31:
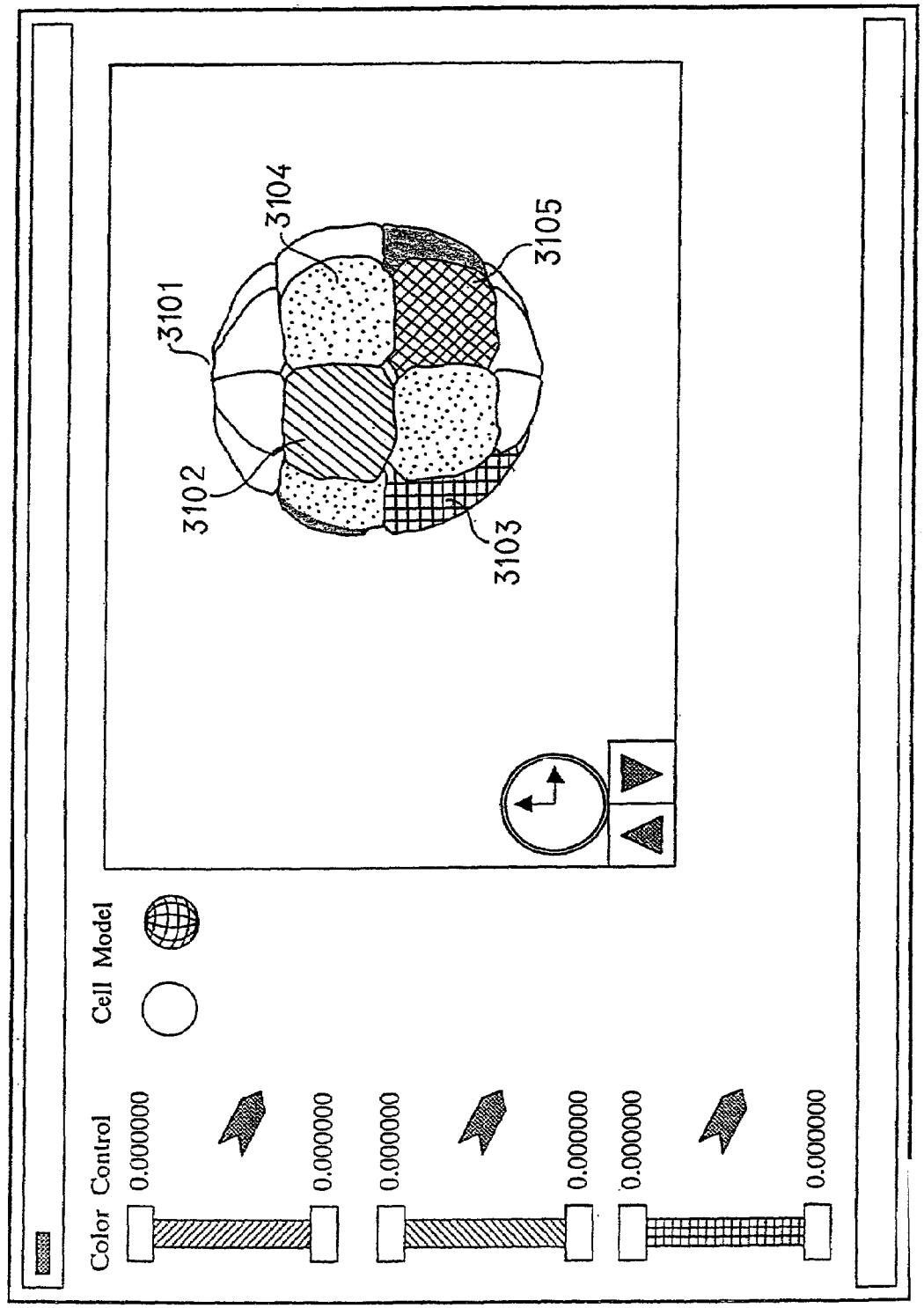
FIG. 31 is a view showing an example in which an expression data of a cell or a site to be observed is mapped on coordination points in a color space of the three primary colors which is based on a data value thereof, and is displayed as color information corresponding to the individual coordination points.

FIG. 31 is a view showing an example in which the expression data of the cell or the site to be observed is mapped on coordination points in the color space of the three primary colors which is based on the data value thereof, and is displayed as color information corresponding to the individual coordination points. Here, the frequencies of expression of the cells in a cell group 3101 are displayed with three different colors 3102 to 3105.

Figure 32:
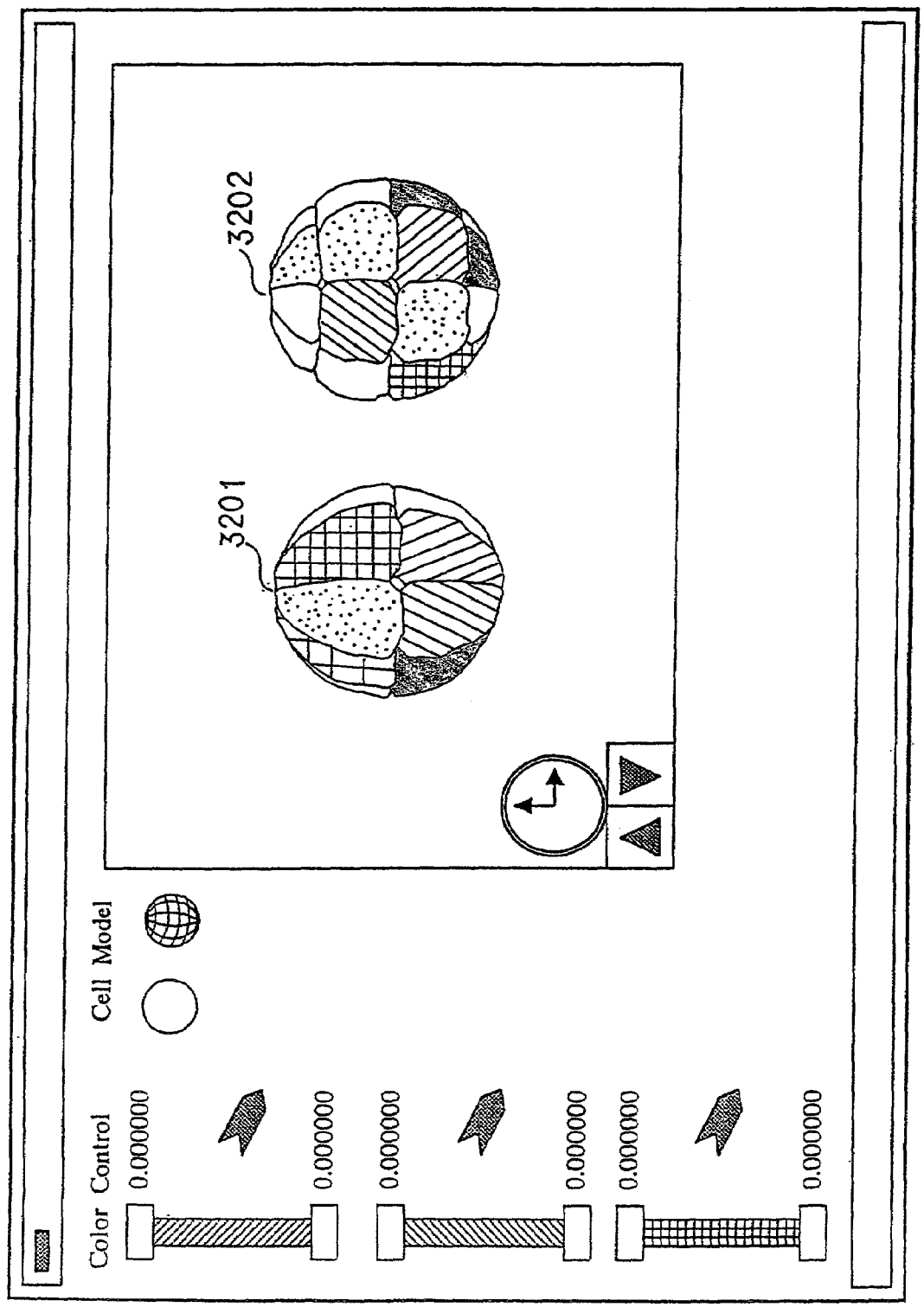
FIG. 32 is a view showing an example in which expression data of two or more cells or sites are mapped on coordination points in a color space of the three primary colors which is based on data values thereof, and are displayed in parallel as color information corresponding to the individual coordination points.

FIG. 32 is a view showing an example in which the expression data of two or more cells or sites are mapped on coordination points in the color space of the three primary colors which is based on the data values thereof, and are displayed in parallel as color information corresponding to the individual coordination points. The frequencies of expression of the cells in two different cell groups 3201 and 3202 are displayed with different colors as in FIG. 31.

Figure 33:
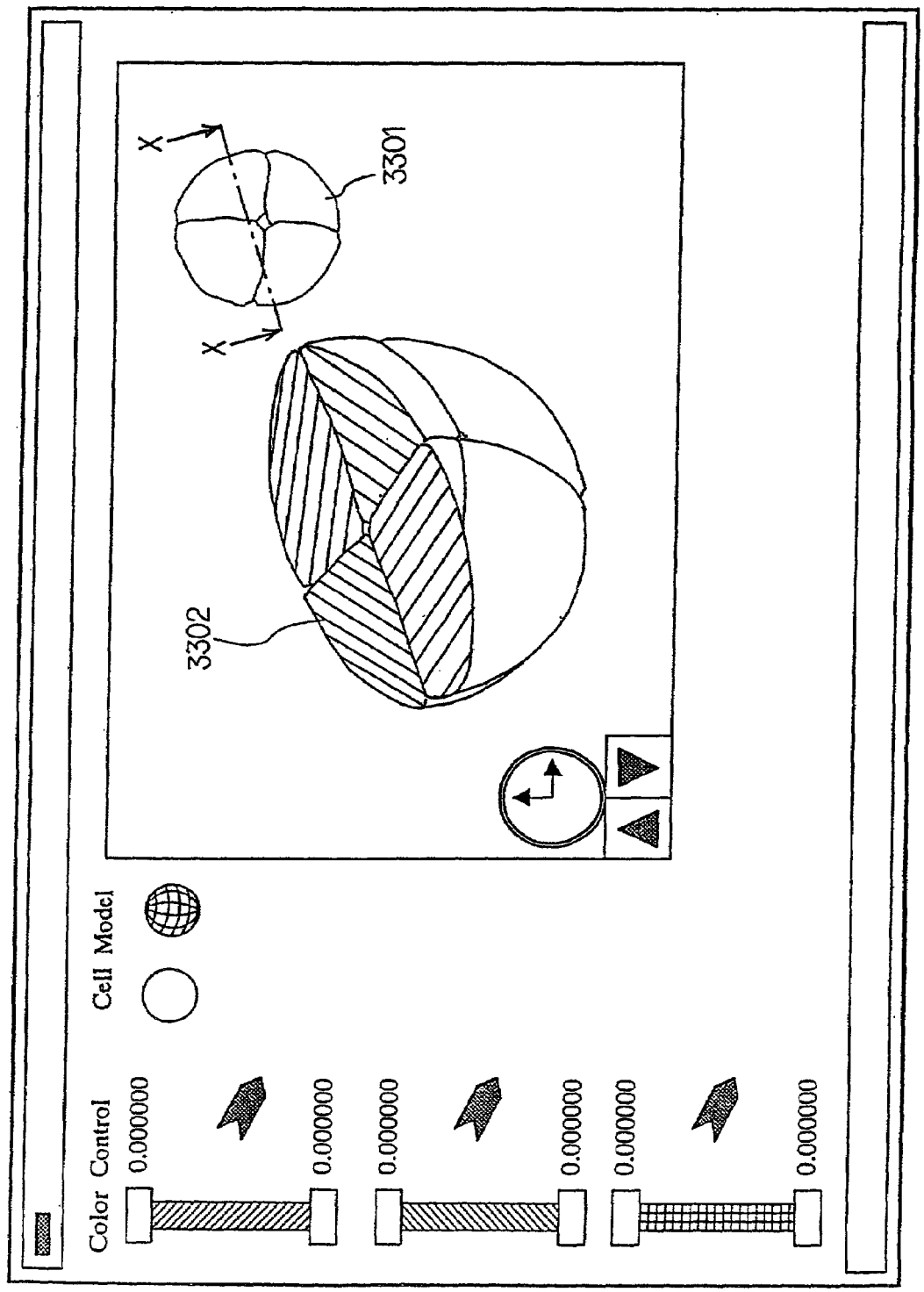
FIG. 33 is a view showing an example in which a three-dimensional image representing an expression phenomenon is cut imaginarily at a plane or a curved plane designated in a three-dimensional space and an image representing the expression phenomenon along the cutting plane is displayed.

FIG. 33 is a view showing an example in which the three-dimensional image representing the expression phenomenon is cut imaginarily at a plane or a curved plane designated in the three-dimensional space and the image representing the expression phenomenon along the cutting plane is displayed. Here, illustrated is an example of an image of a cutting plane 3302 when a three-dimensional image representing the expression phenomenon 3301 is cut imaginarily at an X—X plane.

Figure 34:
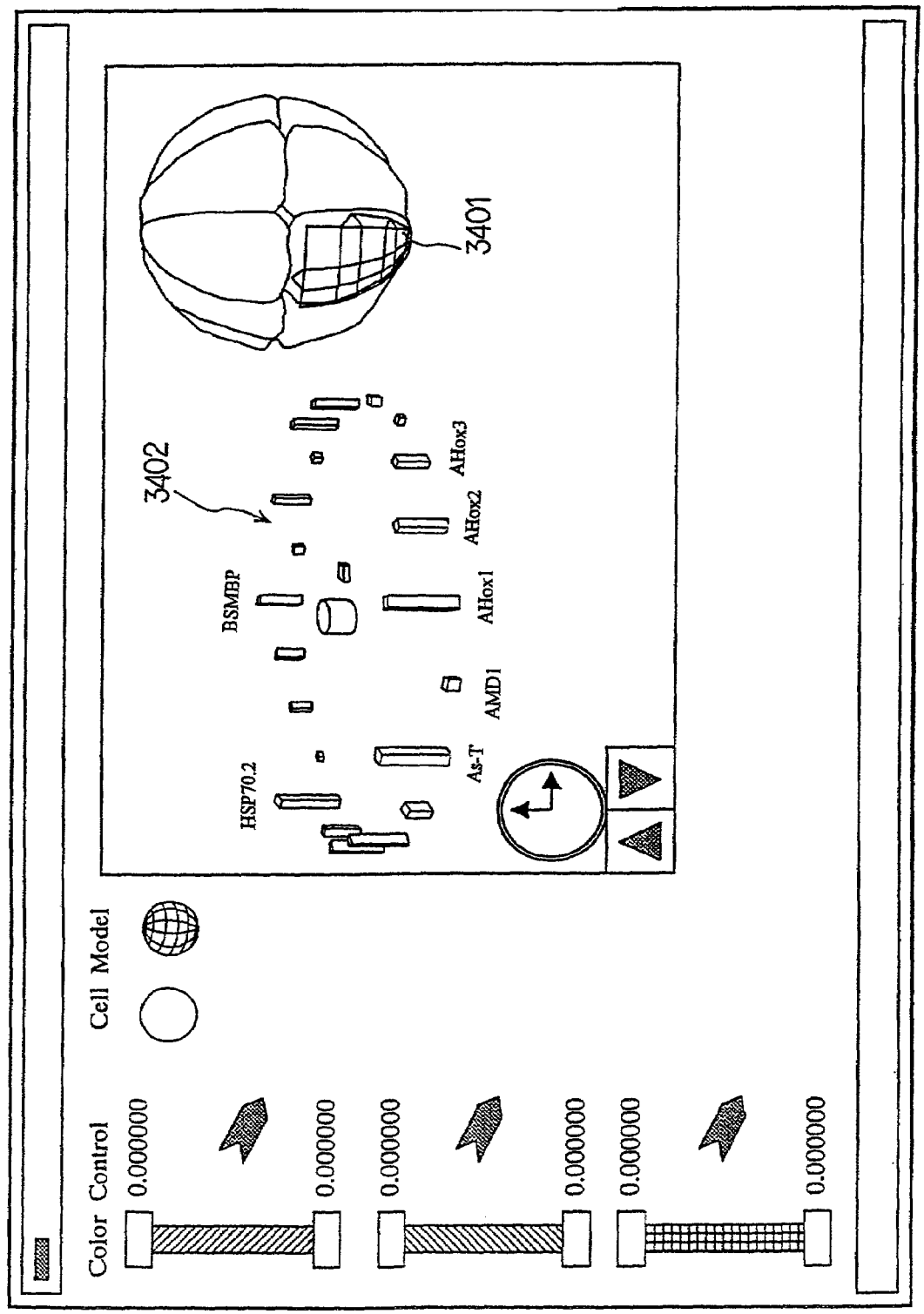
FIG. 34 is a view showing an example in which information about the gene expressed in a designated cell or site is displayed as graphics, in response to an operation that designates the cell or site on a three-dimensional image representing the expression phenomenon.

FIG. 34 is a view showing an example in which information about the gene expressed in the designated cell or site is displayed as graphics, in response to an operation that designates the cell or site on the three-dimensional image representing the expression phenomenon. Here, when a site 3401 is designated on the three-dimensional image representing the expression phenomenon, the information about the gene expressed in the site 3401 is displayed as a cylindrical graph 3402 as in FIG. 1.

Figure 35:
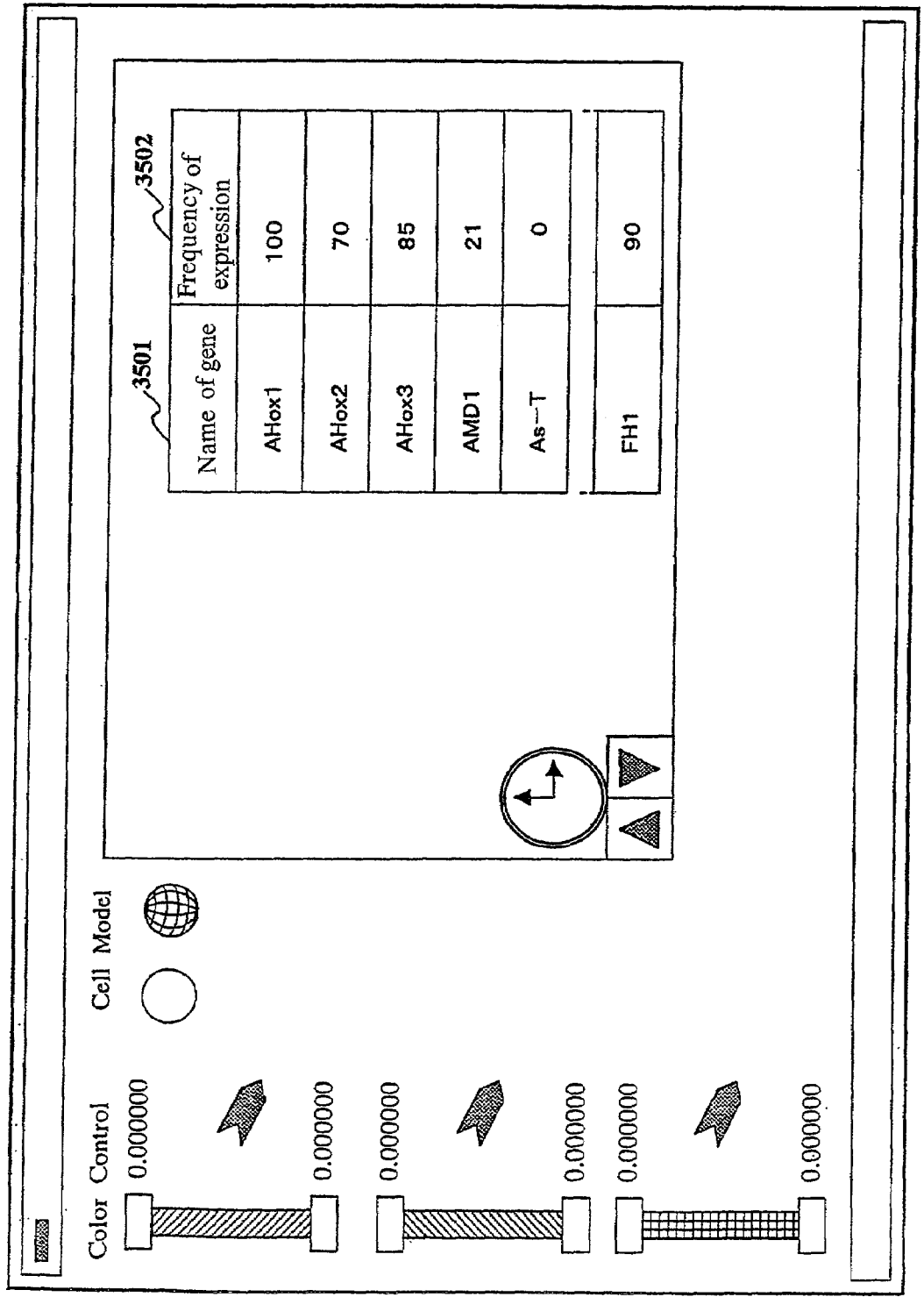
FIG. 35 is a view showing an example in which information about the gene is displayed as a string of characters in place of the cylindrical graph in FIG. 34, the information being formed of a name of a gene and a frequency of expression.

FIG. 35 is a view showing an example in which information about the gene is displayed as a string of characters in place of the cylindrical graph in FIG. 34, the information being formed of a name of a gene 3501 and a frequency of expression 3502.

Figure 36:
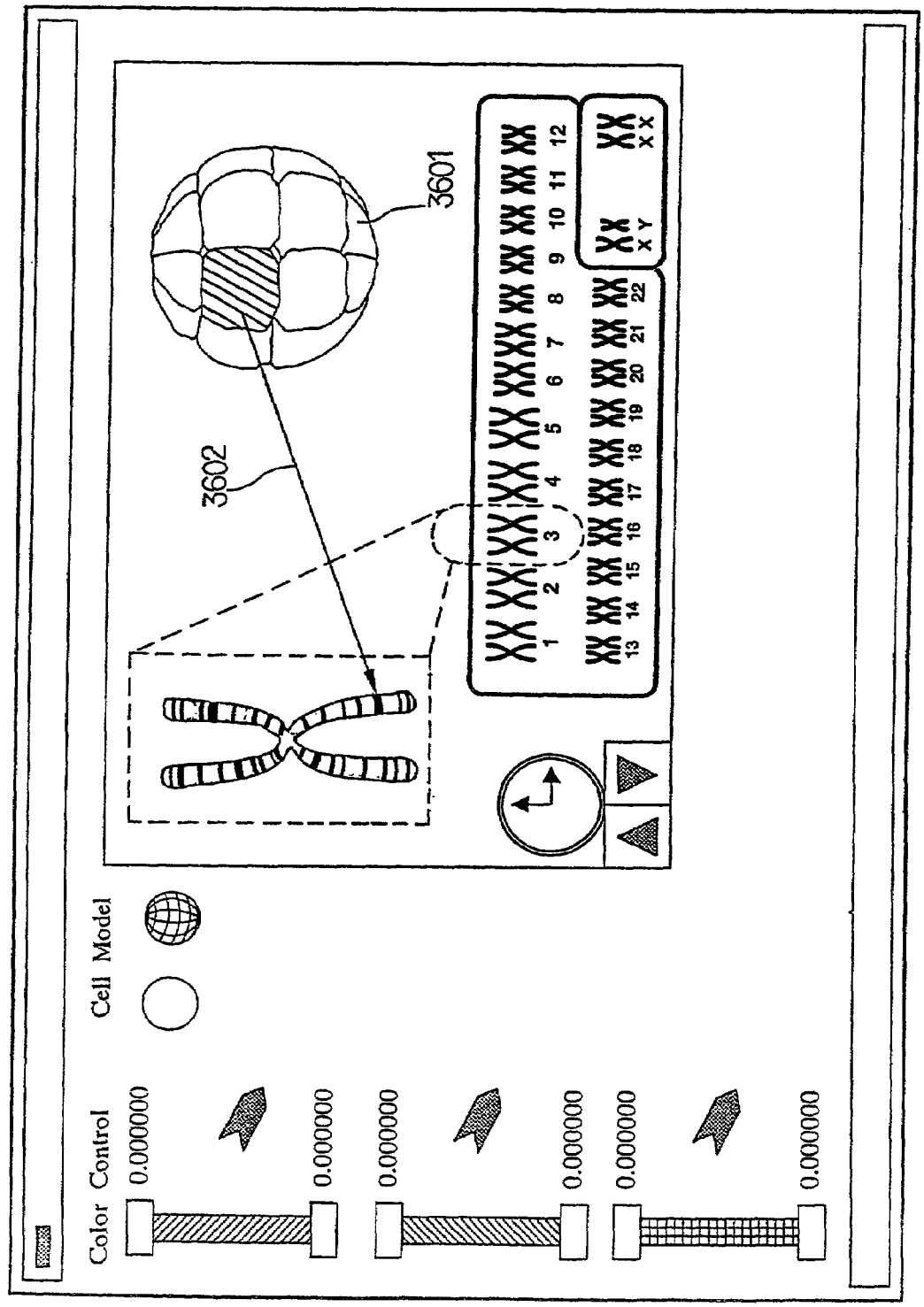
FIG. 36 is a view showing an example in which a three-dimensional image representing an expression phenomenon and a position of a gene on a gene map that causes expression are coordinated and displayed in a predetermined display format.

FIG. 36 is a view showing an example in which the three-dimensional image representing the expression phenomenon and the position of the gene on the gene map that causes expression are coordinated and displayed in a predetermined display format. Here, a three-dimensional image representing the expression phenomenon 3601 and the position of the gene on the gene map that causes expression are connected to each other by an arrow 3602. Alternatively, the subject area may be displayed at high luminosity or be blinked rather than being displayed along with the arrow.

According to the present embodiment described above, it is possible to display (print), in a format directly appealing to the eyes or sense of a researcher, information indicative of gene expression occurring with time to assist the researcher with easy elucidation of a gene network mechanism.

Figure 37:
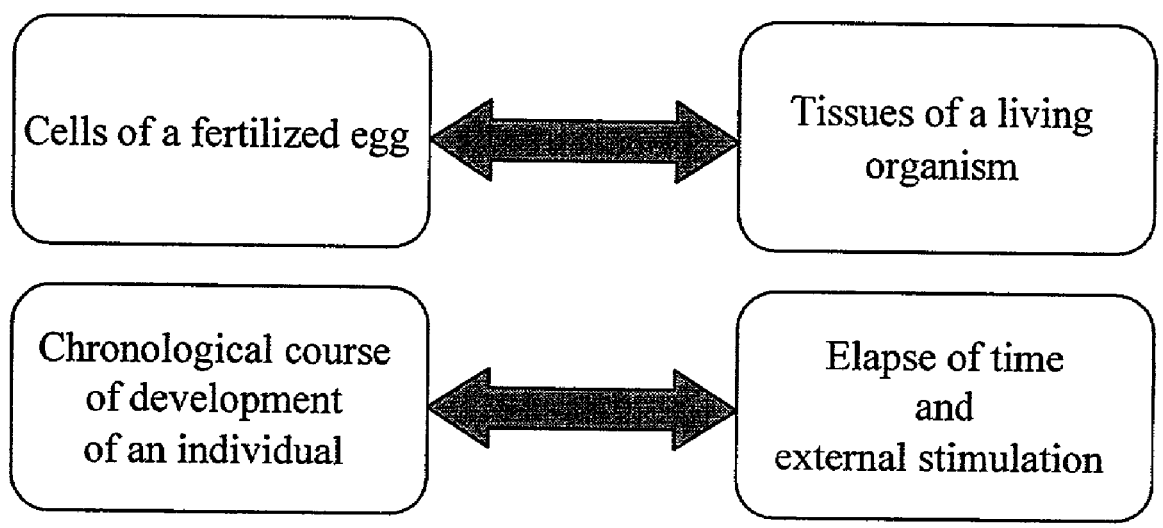
FIG. 37 is a view for use in describing an exemplified application of a system that simulates development of fertilized eggs.

While the embodiment has been described in conjunction with the system that simulates development of fertilized eggs, it may be applied easily to systems for observing various expression phenomena in living matters using similar procedures when association is made among cells of a fertilized egg and tissues of a living organism, a chronological course of development of an individual and an elapse of time and external stimulation, and chronological course of an individual as is shown in FIG. 37.

Figure 38:
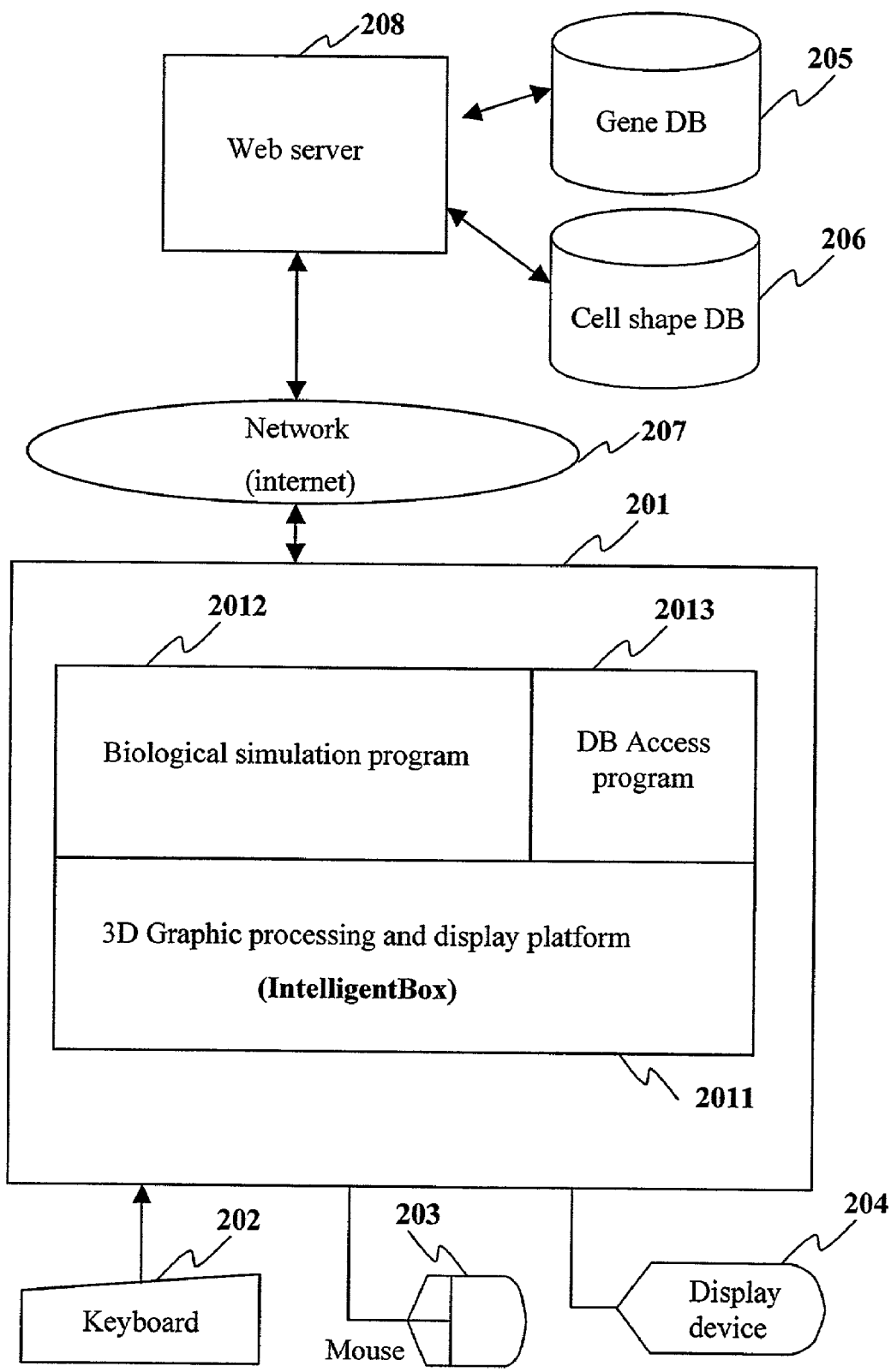
FIG. 38 is a configuration diagram showing another embodiment of a system implementing the present invention.

Furthermore, as shown in FIG. 38, the gene database 205 and the cell shape database 206 may be managed under the control of a Web server 208. The computer 201 may access the gene database 205 and the cell shape database 206 through a network 207 such as the Internet to display the expression phenomenon on the display device 204.

In such a case, either one or both of the gene database 205 and the cell shape database 206 may be accessible directly from the computer 201 without any network.

Furthermore, the gene database 205 and the cell shape database 206 may be managed under the control of separate Web servers and accessed through the network. In addition, the processing unit for producing the three-dimensional image of a shape of the living matter and the processing unit for producing a three-dimensional image representing an expression phenomenon in various scales may be distributed to separate computers or servers.

In FIG. 38, the identical components and parts to those in FIG. 2 are designated using the same reference numerals.

Figure 39:
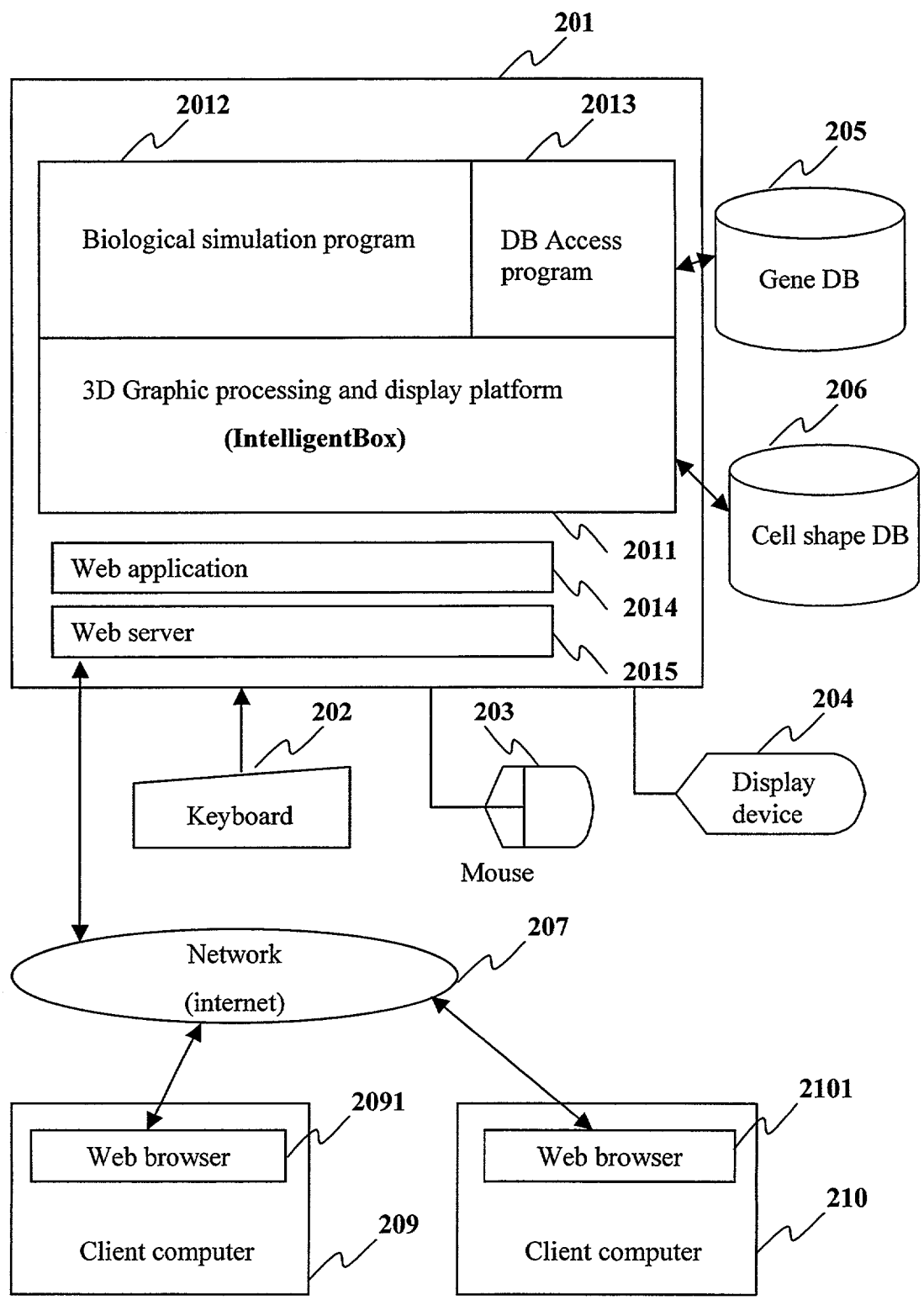
FIG. 39 is a configuration diagram showing yet another embodiment of a system implementing the present invention.

As shown in FIG. 39, the computer 201 may generate the three-dimensional image representing the expression phenomenon in response to a request from the client computer 209 and 210 through a network 207 and send it back to the requesting computer to display it on the screen of the display device of that client computer.

In this case, when the Internet is used, the client computers 209 and 210 has Web browsers 2091 and 2101 installed therein. The computer 201 has an Web application 2014 that converts a three-dimensional image generated by a biological simulation program 2012 into a data in the HTML format, and a Web server 2015 that transmits the data in the HTML format to the network 207.

Here, the keyboard 202 or the mouse 203 associated with the computer 201 may be used to designate a site of a living matter, designate a cell, or the designate the viewpoint of an observer, to the biological simulation program 2012. Furthermore, a keyboard or a mouse (not shown) associated with the client computer 209 or 210 may be used to provide a command or a designation while looking at the screen of the Web browser.

Moreover, in such a client-server based system, either one or both of the gene database 205 and the cell shape database 206 may be associated with a computer that is different from the computer 201.

INDUSTRIAL APPLICABILITY

As apparent from the descriptions made above, according to the present invention, it is possible to display (print), in a format directly appealing to the eyes or sense of a researcher, information indicative of gene expression occurring with time to assist the researcher with easy elucidation of a gene network mechanism.

What is claimed is:

1. A method for displaying a gene expression phenomenon in one or more living organisms in a system comprising a database that collects, for each cell or each site of said living organisms along a time axis, data indicative of a shape of said cell or site and expression data associated with a degree of expression of the gene expression phenomenon in said cell or site along a time axis; and processing means adapted to obtain said data indicative of the shape and expression data that are collected in said database to visualize and display the gene expression phenomenon on a display screen, wherein said method comprising:

displaying as a three-dimensional image on the display screen a shape of said living organisms of which the gene expression phenomenon is observed;

setting a viewpoint by a user via a keyboard or a mouse on a three-dimensional space where the gene expression phenomenon in said living organisms displayed is to be observed;

reading the gene expression data of said cell or site of said living organisms out of said database, creating a plurality of three-dimensional images representing the gene expression phenomenon at the viewpoint set at said second step or at a fixed viewpoint, to display at least one of said three-dimensional images in multiple tones using one color or multiple colors, each of the tones corresponding to a degree of expression of the gene expression phenomenon; and simulating gene expression data by analyzing actual gene expression data and chronologically displaying a simulated change in shape of said cell or site of said living organisms caused by an external stimulation artificially incurred by altering simulation parameters according to a planned experiment and a change in shape of a cell or site caused by internal activities of said cell or site of said living organisms; and displaying an animation of a three-dimensional image representing the gene expression phenomenon from a certain viewpoint at a certain instant of time.

2. A method for displaying a gene expression phenomenon in one or more living organisms in a system comprising a database that collects, for each cell or each site of said living organisms along a time axis, data indicative of a shape of said cell or site and expression data associated with a degree of expression of the gene expression phenomenon in said cell or site along a time axis; and processing means adapted to obtain said data indicative of the shape and expression data that are collected in said database to visualize and display the gene expression phenomenon on a display screen, wherein said method comprising:

displaying as a three-dimensional image on the display screen a shape of said living organisms of which the gene expression phenomenon is observed;

setting a viewpoint by a user via a keyboard or a mouse on a three-dimensional space where the gene expression phenomenon in said living organisms displayed is to be observed;

reading the gene expression data of said cell or site of said living organisms out of said database, creating a plurality of three-dimensional images representing the gene expression phenomenon at the viewpoint set at said second step or at a fixed viewpoint, to display at least one of said three-dimensional images in multiple tones using one color or multiple colors, each of the tones corresponding to a degree of expression of the gene expression phenomenon;

displaying in parallel on the display screen three-dimensional images representing expression phenomena for each cell or site of said living organisms of multiple species; and comparing the three-dimensional images representing the gene expression phenomena for each cell or site of said living organisms of multiple species to visually display similarities therebetween.

3. A method for displaying a gene expression phenomenon in one or more living organisms in a system comprising a database that collects, for each cell or each site of said living organisms along a time axis, data indicative of a shape of said cell or site and expression data associated with a degree of expression of the gene expression phenomenon in said cell or site along a time axis; and processing means adapted to obtain said data indicative of the shape and expression data that are collected in said database to visualize and display the gene expression phenomenon on a display screen, wherein said method comprising:

displaying as a three-dimensional image on the display screen a shape of said living organisms of which the gene expression phenomenon is observed;

setting a viewpoint by a user via a keyboard or a mouse on a three-dimensional space where the gene expression phenomenon in said living organisms displayed is to be observed;

reading the gene expression data of said cell or site of said living organisms out of said database, creating a plurality of three-dimensional images representing the gene expression phenomenon at the viewpoint set at said second step or at a fixed viewpoint, to display on the display screen at least one of said three-dimensional images in multiple tones using one color or multiple colors, each of the tones corresponding to a degree of expression of the gene expression phenomenon; and mapping said three-dimensional images of said cell or site along a time axis to display said three-dimensional images on the display screen in one color or multiple colors in various scales depending on a gene expression frequency in said cell or site.

4. A method for displaying a gene expression phenomenon in one or more living organisms in a system comprising a database that collects, for each cell or each site of said living organisms along a time axis, data indicative of a shape of said cell or site and expression data associated with a degree of expression of the gene expression phenomenon in said cell or site along a time axis; and processing means adapted to obtain said data indicative of the shape and expression data that are collected in said database to visualize and display the gene expression phenomenon on a display screen, wherein said method comprising:

displaying as a three-dimensional image on the display screen a shape of said living organisms of which the gene expression phenomenon is observed;

setting a viewpoint by a user via a keyboard or a mouse on a three-dimensional space where the gene expression phenomenon in said living organisms displayed is to be observed;

reading the gene expression data of said cell or site of said living organisms out of said database, creating a plurality of three-dimensional images representing the gene expression phenomenon at the viewpoint set at said second step or at a fixed viewpoint, to display on the display screen at least one of said three-dimensional images in multiple tones using one color or multiple colors, each of the tones corresponding to a degree of expression of the gene expression phenomenon; and mapping three-dimensional images of two or more cells or sites on coordination points along an axis to display said three-dimensional images on the display screen in one color or multiple colors in various scales of a change in gene expression frequency in said cells or sites in parallel.

5. A method for displaying a gene expression phenomenon in one or more living organisms in a system comprising a database that collects, for each cell or each site of said living organisms along a time axis, data indicative of a shape of said cell or site and expression data associated with a degree of expression of the gene expression phenomenon in said cell or site along a time axis; and processing means adapted to obtain said data indicative of the shape and expression data that are collected in said database to visualize and display the gene expression phenomenon on a display screen, wherein said method comprising:

displaying as a three-dimensional image on the display screen a shape of said living organisms of which the gene expression phenomenon is observed;

setting a viewpoint by a user via a keyboard or a mouse on a three-dimensional space where the gene expression phenomenon in said living organisms displayed is to be observed;

reading the gene expression data of said cell or site of said living organisms out of said database, creating a plurality of three-dimensional images representing the gene expression phenomenon at the viewpoint set at said second step or at a fixed viewpoint, to display at least one of said three-dimensional images in multiple tones using one color or multiple colors, each of the tones corresponding to a degree of expression of the gene expression phenomenon; and organizing and displaying a three-dimensional image of the expression phenomenon and a position on a three-dimensional gene map of a gene that causes the expression phenomenon.

6. A method for displaying a gene expression phenomenon in one or more living organisms in a system comprising a database that collects, for each cell or each site of said living organisms along a time axis, data indicative of a shape of said cell or site and expression data associated with a degree of expression of the gene expression phenomenon in said cell or site along a time axis; and processing means adapted to obtain said data indicative of the shape and expression data that are collected in said database to visualize and display the gene expression phenomenon on a display screen, wherein said method comprising:
- displaying as a three-dimensional image on the display screen a shape of said living organisms of which the gene expression phenomenon is observed;
- setting a viewpoint by a user via a keyboard or a mouse on a three-dimensional space where the gene expression phenomenon in said living organisms displayed is to be observed;
- reading the gene expression data of said cell or site of said living organisms out of said database, creating a plurality of three-dimensional images representing the gene expression phenomenon at the viewpoint set at said second step or at a fixed viewpoint, to display at least one of said three-dimensional images in multiple tones using one color or multiple colors, each of the tones corresponding to a degree of expression of the gene expression phenomenon; and
- organizing and displaying three-dimensional images of the expression phenomenon of a gene in two or more cells or sites and a position on a three-dimensional gene map of a gene that causes the expression phenomenon.

7. A method for displaying a gene expression phenomenon in one or more living organisms in a system comprising a database that collects, for each cell or each site of said living organisms along a time axis, data indicative of a shape of said cell or site and expression data associated with a degree of expression of the gene expression phenomenon in said cell or site along a time axis; and processing means adapted to obtain said data indicative of the shape and expression data that are collected in said database to visualize and display the gene expression phenomenon on a display screen, wherein said method comprising:
- displaying as a three-dimensional image on the display screen a shape of said living organisms of which the gene expression phenomenon is observed;
- setting a viewpoint by a user via a keyboard or a mouse on a three-dimensional space where the gene expression phenomenon in said living organisms displayed is to be observed;
- reading the gene expression data of said cell or site of said living organisms out of said database, creating a plurality of three-dimensional images representing the gene expression phenomenon at the viewpoint set at said second step or at a fixed viewpoint, to display at least one of said three-dimensional images in multiple tones using one color or multiple colors, each of the tones corresponding to a degree of expression of the gene expression phenomenon; and
- mapping expression data of a cell or a site of a plurality of genes of one living organism on coordination points along a circumferential path on a plane, said expression data of each of the plurality of genes being shown as a bar with a height corresponding to a degree of one respect of gene expression phenomenon.

* * * * *